United States Patent
Pitner et al.

(10) Patent No.: US 7,338,778 B2
(45) Date of Patent: *Mar. 4, 2008

(54) LUMINESCENT METHOD FOR DETERMINING CELL OXYGEN CONSUMPTION

(75) Inventors: J. Bruce Pitner, Durham, NC (US); John Jacob Hemperly, Apex, NC (US); Richard D. Guarino, Holly Springs, NC (US); Magdalena Wodnicka, Durham, NC (US); David T. Stitt, Freeland, MD (US); Gregory J. Burrell, Red Lion, PA (US); Timothy G. Foley, Jr., Forest Hill, MD (US); Patrick Shawn Beaty, Selton, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 7 days.

This patent is subject to a terminal disclaimer.

(21) Appl. No.: 10/957,802

(22) Filed: Oct. 4, 2004

(65) Prior Publication Data
US 2005/0191613 A1    Sep. 1, 2005

Related U.S. Application Data

(60) Division of application No. 10/116,777, filed on Apr. 4, 2002, now Pat. No. 6,900,030, which is a division of application No. 09/342,720, filed on Jun. 29, 1999, now Pat. No. 6,395,506, which is a continuation-in-part of application No. 08/715,557, filed on Sep. 18, 1996, now abandoned, which is a continuation-in-part of application No. 08/025,899, filed on Mar. 3, 1993, now Pat. No. 5,567,598, which is a continuation-in-part of application No. 07/687,359, filed on Apr. 18, 1991, now abandoned.

(51) Int. Cl.
*C12Q 1/04*    (2006.01)

(52) U.S. Cl. ............................ 435/34; 435/29; 435/32; 435/69.1

(58) Field of Classification Search .................. 435/34, 435/29, 69.1, 32
See application file for complete search history.

(56) References Cited

U.S. PATENT DOCUMENTS

| | | | | |
|---|---|---|---|---|
| 5,030,420 A | * | 7/1991 | Bacon et al. | 422/82.07 |
| 5,164,796 A | * | 11/1992 | Di Guiseppi et al. | 356/445 |
| 5,511,547 A | * | 4/1996 | Markle et al. | 600/348 |
| 5,567,598 A | * | 10/1996 | Stitt et al. | 435/29 |
| 6,063,617 A | * | 5/2000 | Young et al. | 435/287.5 |
| 6,107,083 A | * | 8/2000 | Collins et al. | 435/288.7 |
| 6,190,612 B1 | * | 2/2001 | Berger et al. | 422/82.07 |
| 6,254,829 B1 | * | 7/2001 | Hartmann et al. | 422/82.06 |
| 6,395,506 B1 | * | 5/2002 | Pitner et al. | 435/32 |
| 6,565,992 B1 | * | 5/2003 | Manners et al. | 428/690 |
| 6,711,423 B2 | * | 3/2004 | Colvin, Jr. | 600/317 |
| 6,900,030 B2 | * | 5/2005 | Pitner et al. | 435/34 |
| 6,967,086 B2 | * | 11/2005 | Guarino et al. | 435/34 |
| 2004/0106209 A1 | * | 6/2004 | Keith | 436/127 |

* cited by examiner

*Primary Examiner*—Ralph Gitomer

(57) ABSTRACT

The present invention relates to methods for detection and evaluation of metabolic activity of eukaryotic and/or prokaryotic cells based upon their ability to consume dissolved oxygen. The methods utilize a luminescence detection system which makes use of the sensitivity of the luminescent emission of certain compounds to the presence of oxygen, which quenches (diminishes) the compound's luminescent emission in a concentration dependent manner. Respiring eukaryotic and/or prokaryotic cells will affect the oxygen concentration of a liquid medium in which they are immersed. Thus, this invention provides a convenient system to gather information on the presence, identification, quantification and cytotoxic activity of eukaryotic and/or prokaryotic cells by determining their effect on the oxygen concentration of the media in which they are present.

15 Claims, 27 Drawing Sheets

LUMINESCENT METHOD FOR DETERMINING CELL OXYGEN CONSUMPTION

This application is a divisional of U.S. application Ser. No. 10/116,777, filed on Apr. 4, 2002, now U.S. Pat. No. 6,900,030, which was a divisional of U.S. application Ser. No. 09/342,720, filed on Jun. 29, 1999, now U.S. Pat. No. 6,395,506, which was a continuation-in-part of U.S. Ser. No. 08/715,557, filed on Sep. 18, 1996, now abandoned, which was a continuation-in-part of U.S. Ser. No. 08/025,899, filed on Mar. 3, 1993, now U.S. Pat. No. 5,567,598, which was a continuation-in-part of U.S. Ser. No. 07/687,359, filed on Apr. 18, 1991 now abandoned.

BACKGROUND OF THE INVENTION

1. Field of the Invention

The invention relates to monitoring of cells in a media.

2. Description of Related Art

Our environment contains a multitude of microorganisms with which we are continuously interacting. These interactions can be beneficial, i.e., fermentations to produce wine, vinegar or antibiotics; neutral; or even harmful, as in the case of infectious diseases. The ubiquitous presence of these microorganisms, thus, creates a continuing need for the detection, identification and study of the presence and metabolic activity of such microorganisms.

While the science of microbiology has changed significantly in the last 25 years, many procedures for the detection, identification and analysis of the behavior of microorganisms are still time consuming. For example, in the area of antimicrobic susceptibility testing nearly half of all testing in hospitals in the United States still use the Bauer-Kirby Disc Method. This method uses the presence or absence of visible growth of the microorganisms to indicate the efficacy of an antimicrobic compound, and generally requires an 18 to 24 hour incubation period to allow for microorganism growth before a result can be obtained. A decrease in the time required to obtain such antimicrobic susceptibility information is needed.

Another popular method for antimicrobic susceptibility testing is the broth micro-dilution method, such as the Sceptor® System for identification and antimicrobic susceptibility testing or organisms (Becton Dickinson Diagnostic Instrumentation Systems, Sparks, Md.). The system uses a disposable plastic panel having a plurality of low volume cupulas (ca. 0.4 ml per cupula), each containing a different test compound or a different concentration of a test compound dried on the cupula surface. The organism to be tested is suspended in the desired testing medium, and aliquots are delivered to the individual cupulas of the test panel. The reagent dried on the panel dissolves in the sample, and the system is then incubated overnight (18 to 24 hrs.) to allow sufficient time for the organisms to interact with the reagent and for visible growth to appear. The panel is subsequently examined visually for the presence or absence of growth, thereby obtaining information on the susceptibility of the organism undergoing testing. Additional wells aid in identifying the organism. However, this test method suffers from the drawback of also requiring a long incubation period.

One approach to the reduction of the incubation time is to monitor metabolic activity of the microorganisms, rather than growth of colonies. Many approaches have been reported in the attempt to rapidly and accurately monitor such metabolic activity.

For example, apparatus utilizing light scattering optical means have been used to determine susceptibility by probing the change in size or number of microorganisms in the presence of various antimicrobic compounds. Commercial instruments utilizing these principles are exemplified by the Vitec System (BioMerieux Corp.). This system claims to yield information on antimicrobic susceptibility of microorganisms within 6 hours for many organism and drug combinations. Other combinations can require as long as 18 hours before the antimicrobic susceptibility of the organism can be determined by this machine.

Additionally, modifications of the Bauer-Kirby procedure have been developed which allow certain samples to be read in four to six hours. However, such a system is "destructive" in nature, requiring the spraying of a developing solution of a color forming dye onto the test plate. Re-incubation and reading at a later time is, thus, not possible and if the rapid technique fails, the experiment cannot be continued for a standard evaluation at a later time.

A bioluminescent method based on the quantity of ATP present in multiplying organisms has been described as yielding results of antimicrobic susceptibility testing in four and half hours for certain compositions (Wheat et al.). However, the procedure tends to be cumbersome and broad applicability has not been shown.

Other approaches have involved monitoring of microbial oxygen consumption by the measurement of pH and/or hemoglobin color change, or by the use of dyes such as triphenyltetrazolium chloride and resazurin, that change color in response to the total redox potential of the liquid test medium.

The monitoring of the consumption of dissolved oxygen by microorganisms, as a marker of their metabolism, has been studied for many years. For example, C. E. Clifton monitored the oxygen consumption of microorganisms over a period of several days using a Warburg flask in 1937. This method measured the change in oxygen concentration in a slow and cumbersome manner.

The "Clark" electrode, a newer electrochemical device, is also commonly used to measure dissolved oxygen. Unfortunately, the Clark electrode consumes oxygen during use (thereby reducing the oxygen available to the microorganisms) and the "standard" size electrode is typically used only to measure volumes of 100 mls or greater to prevent the electrode from interfering with the measurements.

A "miniature" Clark electrode has been described, but this electrode is a complicated multi-component part which must, also, be in contact with the solution to be measured. While an oxygen permeable membrane can be used to prevent the electrode components of the device from interacting with the constituents of the test solution, the oxygen must still equilibrate between the test solution and the measurement system and is consumed once it passes the membrane.

Optical systems which can yield oxygen concentration data, have been developed to overcome the shortcomings of the Clark electrode systems. The main advantage of such optical methods is that the instrumentation required to determine quantitative value does not itself make physical contact with the test solution. Optical techniques allowing both calorimetric and fluorometric analyses for oxygen to be carried out rapidly and reproducibly are known, and costs for such analyses are often quite low. For example, several luminescent techniques for the determination of oxygen have been described which are based on the ability of oxygen to quench the fluorescence or phosphorescence emissions of a variety of compounds. However, such methods have not been adapted to microbial monitoring or prokaryotic or eukaryotic cell monitoring.

Other systems have been described that provide information on the presence, identity and antimicrobic susceptibility of microorganisms in a period of eight hours or less. Wilkins and Stones in U.S. Pat. No. 4,200,493 disclose a system that uses electrodes and a high impedance potentiometer to determine the presence of microorganisms. In U.S. Pat. No. 3,907,646 Wilkins et al. disclose an analytical method which utilizes the pressure changes in the headspace over a flask associated with microbial growth for the detection and surveillance of the organisms. U.S. Pat. No. 4,220,715 to Ahnell, discloses a system wherein the head space gas above a test sample is passed through an external oxygen detector for determination of the presence of microorganisms. Ahnell, in U.S. Pat. No. 4,152,213, discloses a system for analysis by monitoring the vacuum produced by growing organisms in a closed head space above a test sample. U.S. Pat. No. 4,116,775 to Charles et al. is an example of the use of optical means based on the increase in turbidity or optical density of a growing microbial culture for the detection and monitoring of bacterial growth. A combined electro-optical measurement of birefringence of a test solution containing microorganisms is described in EPO 0092958 (Lowe and Meltzer).

The increased incidence of tuberculosis and the recent emergence of Multiple Drug Resistant (MDR) strains threatens the ability to control this disease. Therefore, when a strain is resistant to two or more drugs, such as rifampin and isoniazid, the course of treatment increases from 6 months to 24 months, and the cure rate decreases from almost 100% to less than 60%.

*Mycobacterium tuberculosis* (TB) is a slow growing species. Generally, at least three to five weeks of growth on solid or liquid media are required to produce enough cell mass for identification and susceptibility testing. The most commonly used susceptibility method for TB is the Modified Proportion Method (NCCLS M24-T). This method requires an additional three to four weeks of growth before the results are available. The total elapsed time for a find report is typically two months and may be as much as three months.

The BACTEC 460 instrument (Becton, Dickinson and Company, Franklin Lakes, N.J.) can reduce these times considerably. The BACTEC method detects the presence of mycobacteria by their production of radioactive $CO_2$. The BACTEC system can also detect resistant organisms by their continuing production of radioactive $CO_2$ in the presence of antimycobacterial drugs.

It becomes apparent that a wide variety of methods have been applied to the detection and the antibiotic susceptibility testing of microorganisms. Many of these methods can only yield useful data when monitored by instruments dedicated to this task. Thus there exists a need for a system which can allow determinations of the presence and behavior of microorganisms without the requirement of dedicated instrumentation. Further there exists a need for a system that will allow the determination of the effect of a compound such as an antibiotic on a sample of microorganisms in a short time that does not significantly alter the behavior of the microorganisms.

There also currently exists a need for improved methods of measuring eukaryotic and/or prokaryotic cell growth and viability, such as, for example, in the areas of drug discovery and development. An important application for these methods is in testing and quantifying the effects of therapeutic drugs, drug candidates, toxins and chemicals on the growth of cell lines (i.e, cytotoxicity assays). As an example, potential chemotherapeutic drug candidates are frequently tested at a number of concentrations to determine their potency for inhibiting the growth of selected mammalian tumor cell lines.

The most commonly used reagent for eukaryotic (i.e., mammalian) cell cytotoxicity assays is MTT (3-(4,5-dimethylthiazol-2-yl)-2,5-diphenyltetrazolium bromide) ["Rapid Colorimetric Assay for Cellular Growth and Survival: Application to Proliferation and Cytotoxicity Assays", T. Mossmann, J. Immunol. Methods (1983), vol. 65, 55-63]. This tetrazolium salt is reduced within the mitochondria of metabolically active cells to form a colored precipitate (formazan dye). For cytotoxicty measurements, the cells are typically grown in a microwell trays containing various concentrations of drug. MTT is added and incubated with cells for 1-4 hours, the cells are lysed, the formazan dye is resolubilized by thorough mixing and a dose-response curve is obtained from endpoint absorbance measurements. Among disadvantages of this method are the multiple reagent additions which are required. MTT is also susceptible to interferences from some drugs with reducing groups and from precipitation of some drugs, especially those adsorbing light in the visible region. The test itself is non-reversible and further time point readings of the same cell cultures cannot be performed without setting up a separate assay to be used for each time point.

Another redox indicator suggested for cytotoxicity assays is resazurin which is reduced to resorufin in the presence of growing cells. Resazurin is subject to autoreduction in some media which can cause false positive signals. An improved formulation of resazurin with a redox stabilizing buffer known as "Alamar Blue" has been introduced to solve this autoreduction problem in U.S. Pat. No. 5,501,959. This formulation, however, still requires the addition of dye and buffer to the cells and is essentially a non-reversible reduction.

Another method for determining cell viability is to measure uptake of radiolabeled nucleotides such as tritiated thymidine. This test is very sensitive but it is relatively expensive, time-consuming, and requires multiple steps. It also requires the handling and disposal of radioisotopic waste. This type of assay cannot readily be automated or adapted to formats for rapid drug screening purposes.

SUMMARY OF THE INVENTION

It is therefore an object of this invention to provide an improved means to detect the presence of, and to evaluate the metabolic activity of, eukaryotic cells present in a liquid or semi-solid media. It is further an object of this invention to provide a microbial monitoring device or system which can be simply read and visually interpreted, and which permits results to be obtained in a shorter time period than previously attainable, nominally 6 hours or less. Additionally, it is an object of the invention to provide a means for detection and/or monitoring the activity of eukaryotic cells without the use of dedicated instrumentation.

The above and related objects are realized by the processes of the instant invention. These processes utilize a luminescence detection system, and more particularly, a fluorescence detection system wherein the fluorescing sensor compound is one which exhibits a quantifiable degree of quenching when exposed to oxygen. In one embodiment, the sensor compound may be brought into contact with the test sample (either directly or separated by an oxygen permeable membrane) and the fluorescence is measured or observed visually with appropriate aids. In another embodiment, an increase in fluorescence is indicative of respiring aerobic microorganisms, which utilize (and thereby reduce) the oxygen in the sample.

The sensor need not be in direct contact with the test sample. The only requirement is that the test sample and sensor are in a container substantially isolated from atmospheric oxygen so that the sensor can react to the presence/absence of oxygen in the container.

The system can, thus, be used to detect a variety of respiring eukaryotic and/or prokaryotic cells and can be used in cytoxicity assays for the effects of drugs, toxins, or chemicals on eukaryotic and/or prokaryotic cells.

DETAILED DESCRIPTION OF THE INVENTION

Figure 1:
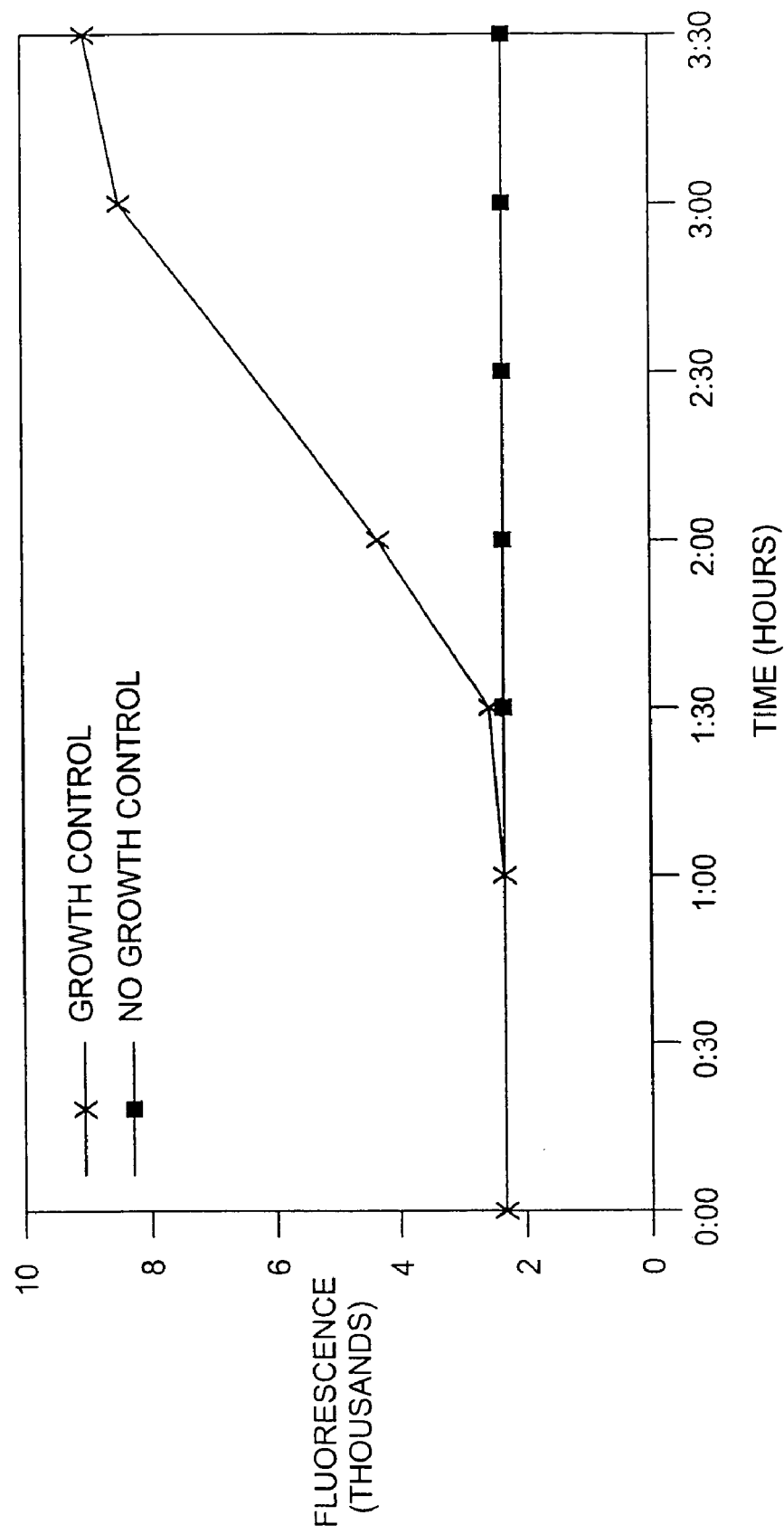
FIG. 1 graphically depicts intensity of fluorescence as a function of time for indicators in contact with broth containing organisms and broth containing no organisms.

The process of this invention presents a quick, easy, and unambiguous method for the measurement and/or detection of respiring aerobic microorganisms and more generally, eukaryotic and/or prokaryotic cells, by measurement or visual observation of luminescence. The term luminescence is intended to include fluorescence and phosphorescence, as well as time-resolved fluorescence and fluorescence lifetime. In a preferred embodiment the luminescent sensor compound can be a fluorescent sensor compound. In the process of the present invention, this compound is irradiated with light containing wavelengths which cause it to fluoresce, and the fluorescence is measured by any standard means, or evaluated visually.

The fluorescent compound must be one which exhibits a large quenching upon exposure to oxygen at concentration ordinarily found in the test liquids (generally 0.4%). While virtually any such compound can be used, preferred fluorescent compounds of this invention are tris-2,2'-bipyridyl ruthenium (II) salts, especially the chloride hexahydrate salt (Ru(BiPy)$_3$Cl$_2$), tris4,7-diphenyl-1,10-phenanthroline ruthenium (II) salts, especially the chloride (salt Ru(DPP)$_3$Cl$_2$), and 9,10-diphenyl anthracene (DPA).

The fluorescent compound must be placed in chemical communication with the oxygen of the test sample to exhibit the quenching. This can be achieved by placing the compound directly in contact with the sample. However, in a preferred embodiment the compound and sample are separated from each other by the interposition of a membrane embedding material permeable to oxygen, and relatively impermeable to the other sample components, between them, thereby preventing the interaction of the sample and the compound. Neither the fluorescent compound nor the membrane in which the fluorescent compound is embedded need be in direct contact with the test sample, broth, or fluid (the compound and sample must be substantially isolated from atmospheric oxygen, thereby preventing any false reading due to the presence of atmospheric oxygen), but still permitting reaction of the compound to the presence or absence of oxygen as a result of respiration of microorganisms.

The system can be allowed to interact unobserved for a predetermined amount of time after which the presence or absence of fluorescence is observed and compared to appropriate control samples, yielding results that are often obtained with a single such observation. A particular benefit of this system, is that the measurement of fluorescence is non-destructive and if after a period of time (e.g. 4 hours) the results are non-conclusive, the system can be re-incubated and read again at a later time. Further, while it is anticipated that the results will be compared with reagent controls, such is by no means necessary, and it is postulated that, by appropriate choice of fluorescent compounds, a skilled technician or technologist would be capable of independently determining whether the results indicate the presence of microbial activity.

The detection of fluorescent intensity can be performed by any means ordinarily used for such measurements, e.g. a fluorometer. Alternatively, the fluorescent intensity can be observed visually and, optionally, compared with a reagent control (e.g. a system containing no live organisms or a system with no added test chemicals). Thus, the methods can be utilized to both provide a quantitative measurement of relative activity, using a fluorometer, or a more qualitative estimate of such activity, by visual inspection.

In a preferred embodiment of this invention, the fluorescent compound is chosen such that it will exhibit little or no fluorescence in the presence of oxygen. This obviates the need for a control, as the person performing the test would interpret any appreciable fluorescence (i.e. beyond that of any nominal background fluorescence) as indicative of the presence of microbial activity. Such results can be obtained by a fluorometer or other measurement means, or preferably, visual inspection, and provide a quick, qualitative estimate of such activity. Preferred fluorescent compounds for this embodiment include Ru(BiPy)$_3$Cl$_2$ and Ru(DPP)$_3$Cl$_2$.

It has also been found that for systems where the compound or compound embedded membrane is in contact with the fluid, test sample, or broth, while the test can be run in systems isolated from atmospheric oxygen, accurate results can also be obtained when the system is left exposed to atmospheric oxygen. In fact, this is desirable when the organisms are to be incubated for periods of time exceeding 2 hours, as they would otherwise tend to consume all the dissolved oxygen in the system and subsequently generate a false reading. Thus, the system of this invention is quite versatile, and can be used in a wide array of conditions.

A further benefit of the instant invention is that a unitized apparatus can be constructed. Briefly, the apparatus comprises a sample containing reservoir, or more commonly a plurality of identical reservoirs adapted to contain a test sample and other such liquid and soluble components (e.g. nutrients, etc.) as may be required by the particular application. The reservoirs also provide a luminescent indicator element which monitors the oxygen levels of the solution. The indicator element of this invention uses a luminescent compound known to show a large quenching of its luminescent emission when exposed to oxygen.

In a preferred embodiment of this invention, the luminescent compound can be mixed and distributed throughout a plastic or rubber phase that is permeable to oxygen gas but relatively impermeable to water and non-gaseous solutes. Silicone rubber is a particularly useful material for this application. When a test solution containing, for example, microorganisms, is placed in such a sample reservoir, the metabolic activity of the organisms causes a reduction in the level of dissolved oxygen in the sample, and the sample will yield a higher luminescent signal upon excitation. Sample liquids not containing microorganisms will not show a decrease in their oxygen levels and will only show low levels of luminescent due to high oxygen quenching of luminescence.

Alternatively, the oxygen sensitive fluorophore or luminescent compound can be in a microencapsulated form or in the form of granules of an oxygen permeable material. It is also anticipated that the fluorophore or luminescent compound can be contained within a separately manufactured component such as a bead, disc, or prongs, which can be separately introduced into the test solution. The use of prongs is particularly advantageous as such prongs can be attached to a lid or other device to permit easy manipulation. In a preferred embodiment, a plurality of prongs can be attached to a single membrane, or other cover and thereby be maintained in an appropriate orientation such that they can simultaneously be placed into the reservoirs of a base containing a plurality of sample reservoirs. By choice of appropriate materials, the prongs can be made impermeable to the indicator molecules and to microorganisms in the sample, but permeable to oxygen.

The fluorophore or luminescent compound can also be in a liquid phase separated from the solution being analyzed by a membrane that is impermeable to the indicator molecules and to microorganisms in the sample but which is permeable to oxygen. Additionally, less-sensitive sensors can be fabricated by using less O$_2$ permeable polymers or by using compounds with shorter excited-state lifetimes.

It is also considered that the luminescent sensor compound, which is an oxygen sensor, can be a phosphorescent compound such as platinum (II) and palladium (II) octaethyl porphyrin complexes immobilized in PMMA (polymethyl methacrylate); CAB (cellulose acetate brityrate); platinum (II) and palladium (II) octaethyl porphyrin ketone complexes immobilized in PVC (polyvinylchloride) and polystyrene.

Further, the methods of this invention can be used to test the susceptibility of a microorganism or eukaryotic and/or prokaryotic cells to a compound, such as an antibiotic, which is capable of severely inhibiting the growth and/or the metabolic activity of organisms. The increase in luminescent signal normally caused by the organism will be suppressed in the presence of such compounds. The behavior of the luminescent signal from a reservoir will demonstrate the ability of the test component to negatively effect the normal oxygen consumption of the organism added to the reservoir.

In addition, any of the embodiments discussed above may be utilized so that the sensor, luminescent compound, or the membrane in which it is embedded need not be in direct contact with the test sample, fluid, or broth in which the microorganisms or eukaryotic and/or prokaryotic cells may be present. In such case, the sensor, compound or membrane in which it is embedded need only be in the same container with the test sample, fluid or broth and that they be substantially isolated from atmospheric oxygen to function as an indicator of the presence or absence of respiring microorganisms, or eukaryotic and/or prokaryotic cells.

It is also apparent that an assay method which is reversible, non-destructive to cells, requires no reagent additions, and poses no additional disposal requirements would be advantageous for cytotoxic drug screening, cellular quantitation, and viability testing.

The present invention describes a method for analyzing and quantifying eukaryotic and/or prokaryotic cells, and, in a preferred embodiment, mammalian cells, based on their consumption of oxygen. Examples of prokaryotes include bacteria and cyanobacteria. This group includes common bacteria such as *Escherichia coli*, widely used in genetic engineering, and both pathogenic and non-pathogenic organisms such as *Mycobacteria, Staphylococcus*, and *Salmonella*. Examples of eukaryotes include protists, fungi, plants and animals. This would include predominantly unicellular organisms, such as yeast and fungi, and multicellular organisms such as insects, reptiles, birds, and mammals. In a preferred embodiment, this includes cells from rodents and from humans and the cell lines derived from them. These examples are not intended to restrict in any way the types of cells that can be analyzed by the present invention.

Optical sensors for determining oxygen concentration based on oxygen's quenching of luminescence have been previously described ["Determination of oxygen concentrations by luminescence quenching of a polymer-immobilized transition-metal complex", Bacon, J. R.; Demas, J. N., Anal. Chem. (1987), 59(23), 2780-5]. These consist of a luminescent dye which is sensitive to oxygen quenching immobilized in an oxygen-permeable membrane. When placed in contact with a liquid media such sensors can respond to changes in oxygen content in the media due to cellular respiration. Consumption of oxygen by living cells in a solution (or fluid or liquid media) decreases the concentration of oxygen within a sensor in contact with the solution. The dye's luminescence increases as the cells consume available oxygen. Such sensors have not previously been described for determining the growth or viability of eukaryotic and/or prokaryotic cells.

Furthermore, the sensor need not be in direct contact with the solution in order to analyze and quantify eukaryotic and/or prokaryotic cells. The only requirement is that the solution and sensor are in a contained area substantially isolated from atmospheric oxygen so that the sensor can react to the presence or absence of oxygen in the contained area.

The present invention describes the use of such oxygen sensors in a microwell tray format for quantitation of eukaryotic and/or prokaryotic cell cultures, and preferably, mammalian cell cultures, and for cytotoxicity assays. The microwell format enables reading with routine luminescence plate readers. This format offers ease of use in a non-destructive assay in which no additional reagents are required. This feature allows cells to be repeatedly monitored since no dyes or indicators are added to or released into the cellular media. The cells grown and monitored in the wells may thus be removed and used for additional assays or subculturing if desired. Because this method is readily adapted to microwell tray formats such as 96 well and 384 well plates, the method is especially useful for high throughput screening of drugs, toxins and other chemicals to determine their cytotoxic activity.

Examples of drugs and toxins which can be utilized in the process of the present invention gallium nitrate, procarbazine, fludarabine, vinblastine, streptozotocin, pentostatin, mitoxantrone, hydroxyurea, piperazinedione, MGBG, 5-azacytidine, bisantrene, cytarabin, colchicine, cladribin, amsacrine, 6-thioguanine, aclarubicin, cisplatin, 5-fluorourocil, bleorycin, mitomycin C, actinomycin D, methotrexate, mechlorethamine, melphalan, docetaxel, epirubicin, etoposide, vincristin, doxorubicin, teniposide, trimetrexate, topotecan, CPT 11, paclitaxel, gemcitabin, thymidine, acivicin, spirogermanium, cyclocytidine, zinostatin, flavone acctate, diglycoaldehyde, deazauridine, anguidine, PALA, aphidicolin, L-alanosine, maytansine, DQ-1, camptothecin, cremophor EL, homoharringtonine, sodium azide, DQ-2, and $HgCl_2$, but this is not intended to be limited to such drugs and toxins and can include any drug or toxin which can be utilized in the present invention.

Examples of chemicals, including components, compounds, amino acids, vitamins, salts, proteins and others, which can be utilized in the process of the present invention include magnesium chloride, glucose, D-galactose, L-valine, glutamine, phenylalanine, arginine, cystine, glutamine, histidine, isoleucine, leucine, lysine, methionine, threonine, tryptophan, tyrosine, valine, biotin, choline, folate, nicotinamide, pantothenate, pyridoxal, thiamine, riboflavin, sodium chloride, potassium chloride, $NaH_2PO_4$, $NaHCO_3$, calcium chloride, insulin, transferrin, and specific growth factors such as recombinant human epidermal growth factor, hydrocortisone, fibroblast growth factor, vascular endothelial growth factor, ascorbic acid (vitamin C), insulin-like growth factor and heparin, but this is not intended to be limited to such chemicals and can include any chemical which can be utilized in the present invention.

In a preferred embodiment, the oxygen sensor plates were prepared using 96 well microtiter plates following general methods described herein. These plates used the fluorescent dye 1,7-diphenyl-1,10-phenanthroline ruthenium (II) 'chloride adsorbed to silica gel and embedded in a silicone matrix.

Figure 10:
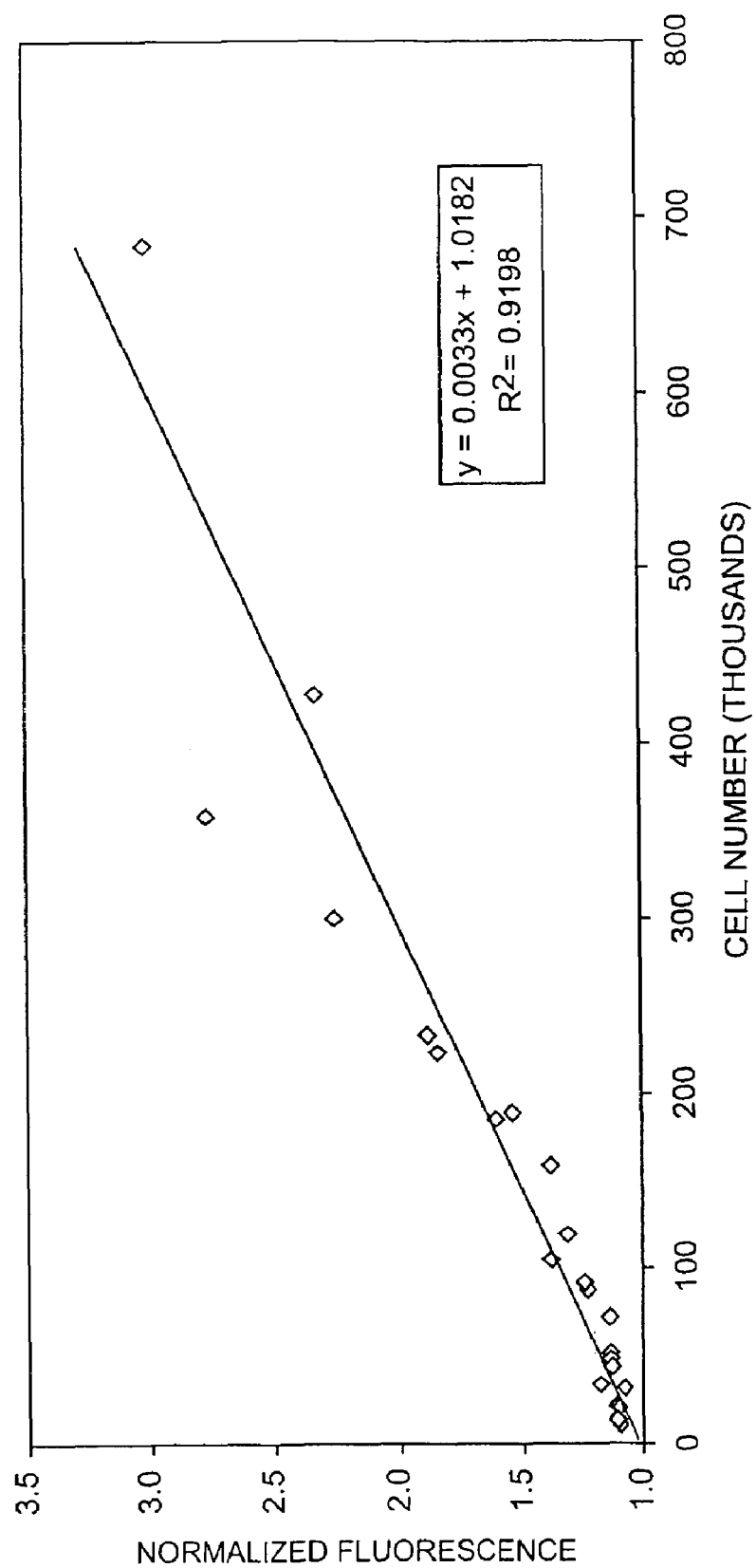
FIG. 10 graphically depicts intensity of fluorescence by plotting fluorescence signal vs. cell number for HL60 cells growing in oxygen sensor plates, wherein the cell number was determined by averaged hemacytometer readings.
Figure 11:
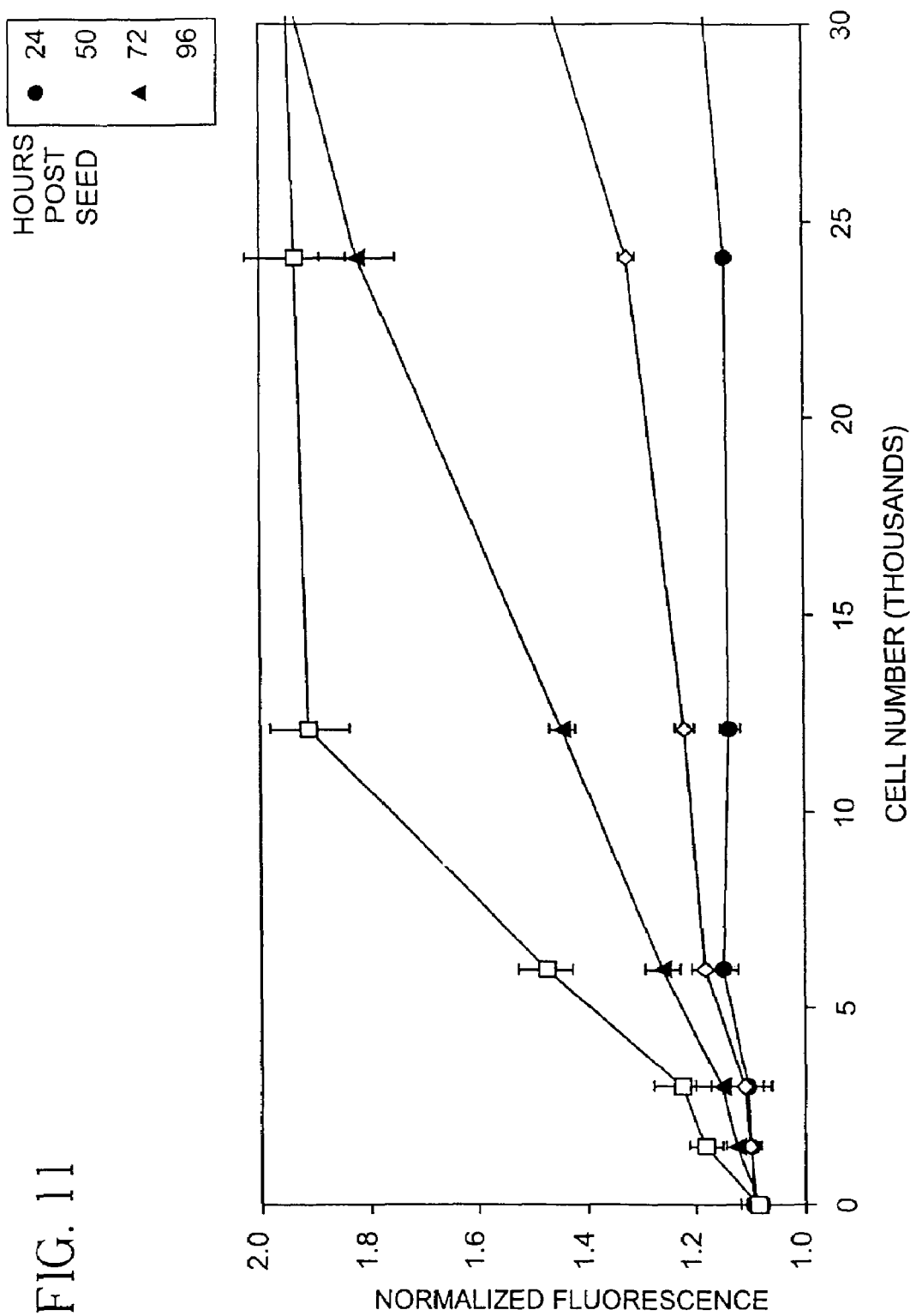
FIG. 11 graphically depicts intensity of fluorescence by plotting fluorescence signal vs. the initial cell number for U937 cells grown in oxygen sensor plates.

The sensor plates may be used to quantify, for example, the number of viable eukaryotic cells in media using a standard microplate fluorimeter. Results are shown in FIG. 10 for a preferred embodiment for quantifying mammalian cells, for absolute number of cells during a growth assay vs. the normalized fluorescent signal (the relative signal for each well at a given time point divided by the initial fluorescence of the well is referred to as "normalized fluorescence"). The absolute cell number was determined by hemacytometer at the time of each reading. An alternative quantitation method is shown in FIG. 11 where the initial cell number (i.e. "seeded cell number") may be inferred from the increase in normalized fluorescence over time.

Figure 12:
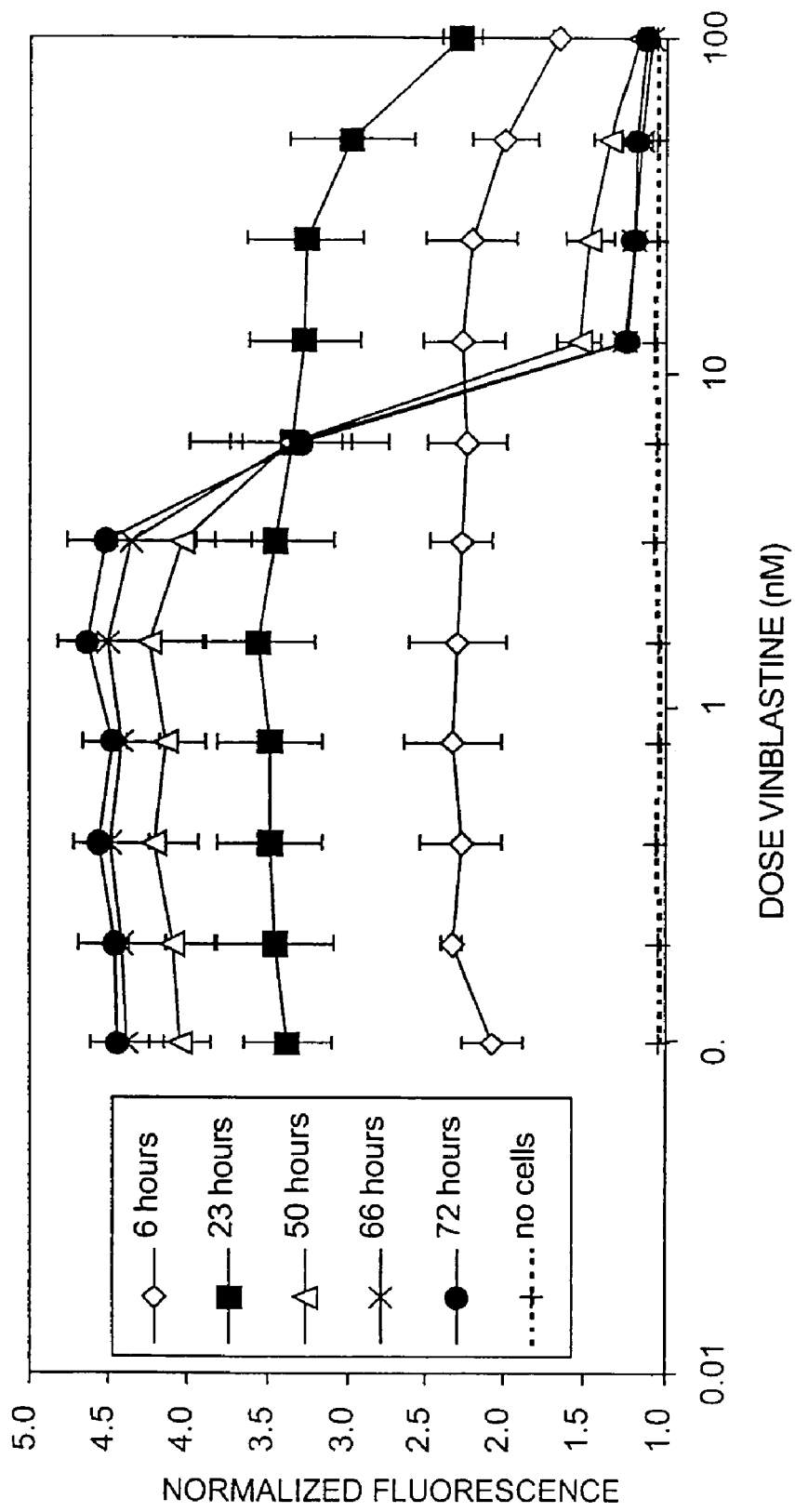
FIG. 12 graphically depicts intensity of fluorescence by plotting fluorescence vs. concentration of vinblastine in a cytotoxicity assay with HL60 cells at selected time points in an oxygen sensor plate.
Figure 13:
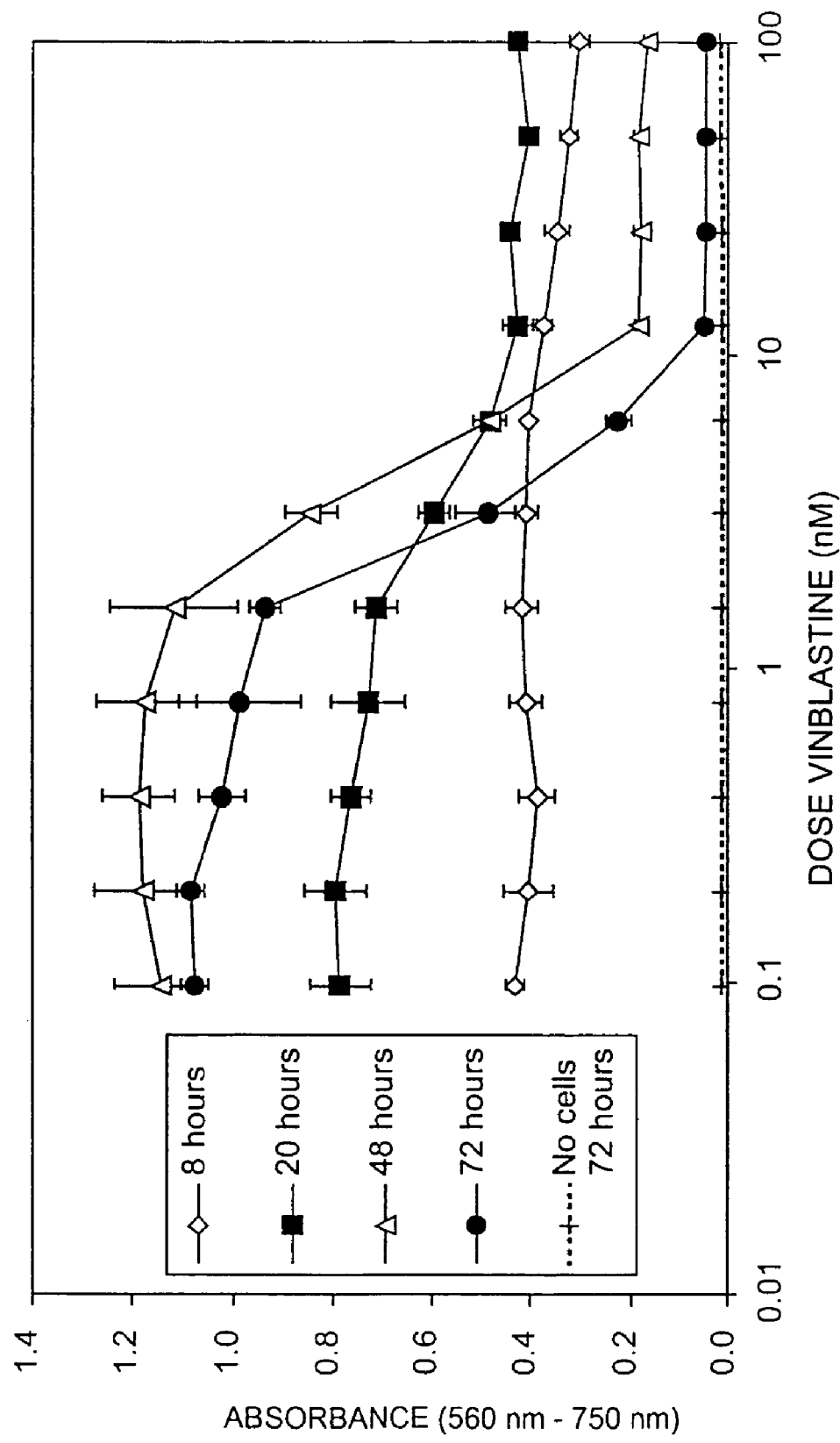
FIG. 13 graphically depicts absorbance, by plotting absorbance vs. concentration of vinblastine in a cytotoxicity assay using MTT with HL60 cells.
Figure 14:
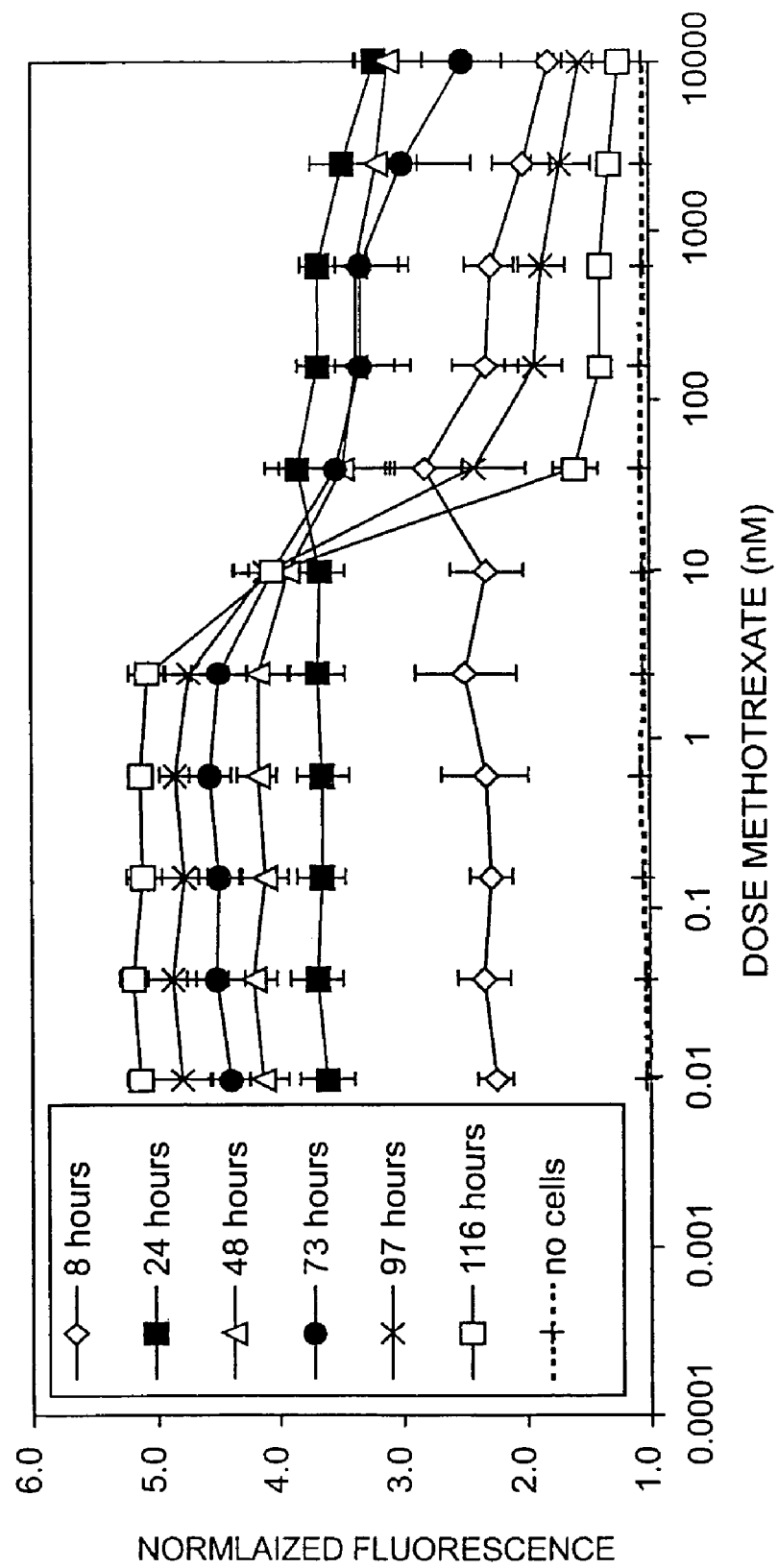
FIG. 14 graphically depicts intensity of fluorescence by plotting fluorescence vs. concentration of methotrexate in a cytotoxicity assay with HL60 cells at selected time points in an oxygen sensor plate.
Figure 15:
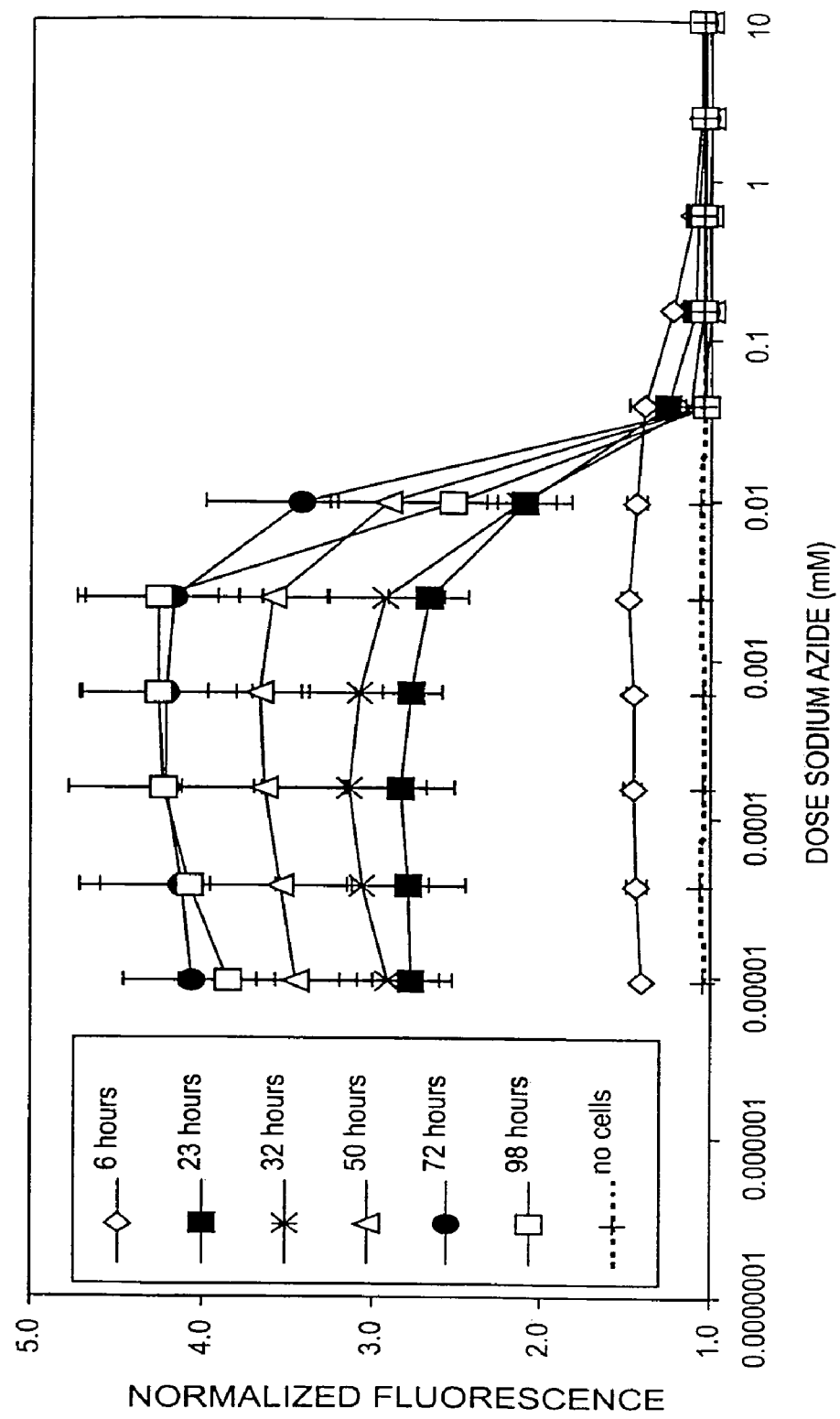
FIG. 15 graphically depicts intensity of fluorescence by plotting fluorescence vs. concentration of sodium azide in a cytotoxicity assay with HL60 cells at selected time points in an oxygen sensor plate.
Figure 16:
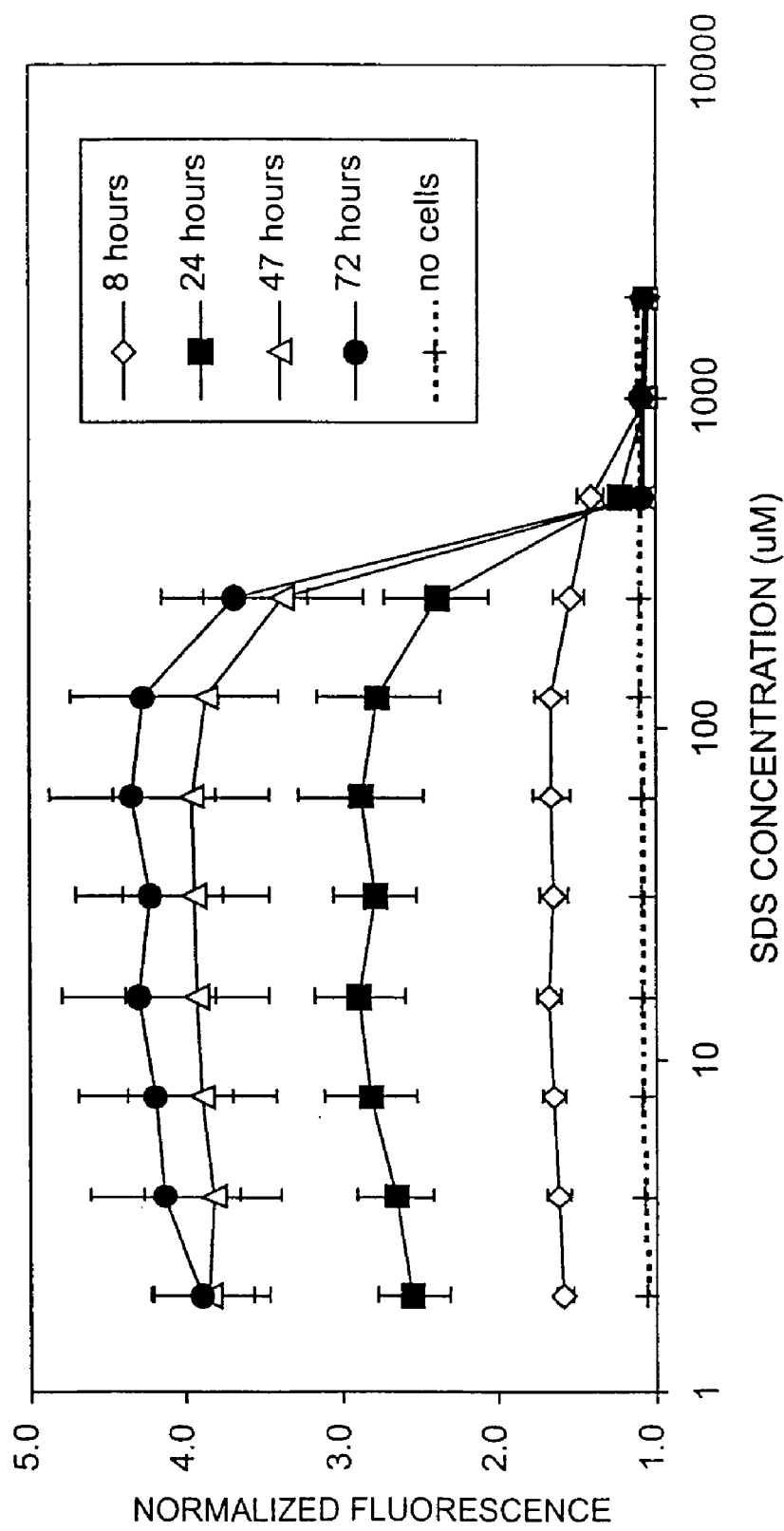
FIG. 16 graphically depicts intensity of fluorescence by plotting fluorescence vs. concentration of SDS in a cytotoxicity assay with HL60 cells at selected time points in an oxygen sensor plate.

FIGS. 12 and 14-16 demonstrate selected cytotoxicity assays with the oxygen sensor plates in which an equivalent number of cells in media were distributed in each well. Serial dilutions of selected drugs and toxins were prepared and added to the wells. Incubation of the plates for the indicated periods of time produced dose-response curves from which $IC_{50}$ results can be obtained. To demonstrate functional equivalence to existing cytotxicity assays, parallel experiments were performed using MTT to obtain dose-reponse curves for the same set of drugs. An example, the MTT dose-response curve of vinblastine with HL60 cells, is shown in FIG. 13. It is important to note that the MTT data in FIG. 13 required a separate plate for each of the timepoint curves. The analogous oxygen sensor assay in FIG. 12 demonstrates repeated readings of the same sensor plate to obtain an optimal dose-response curve.

Figure 17:
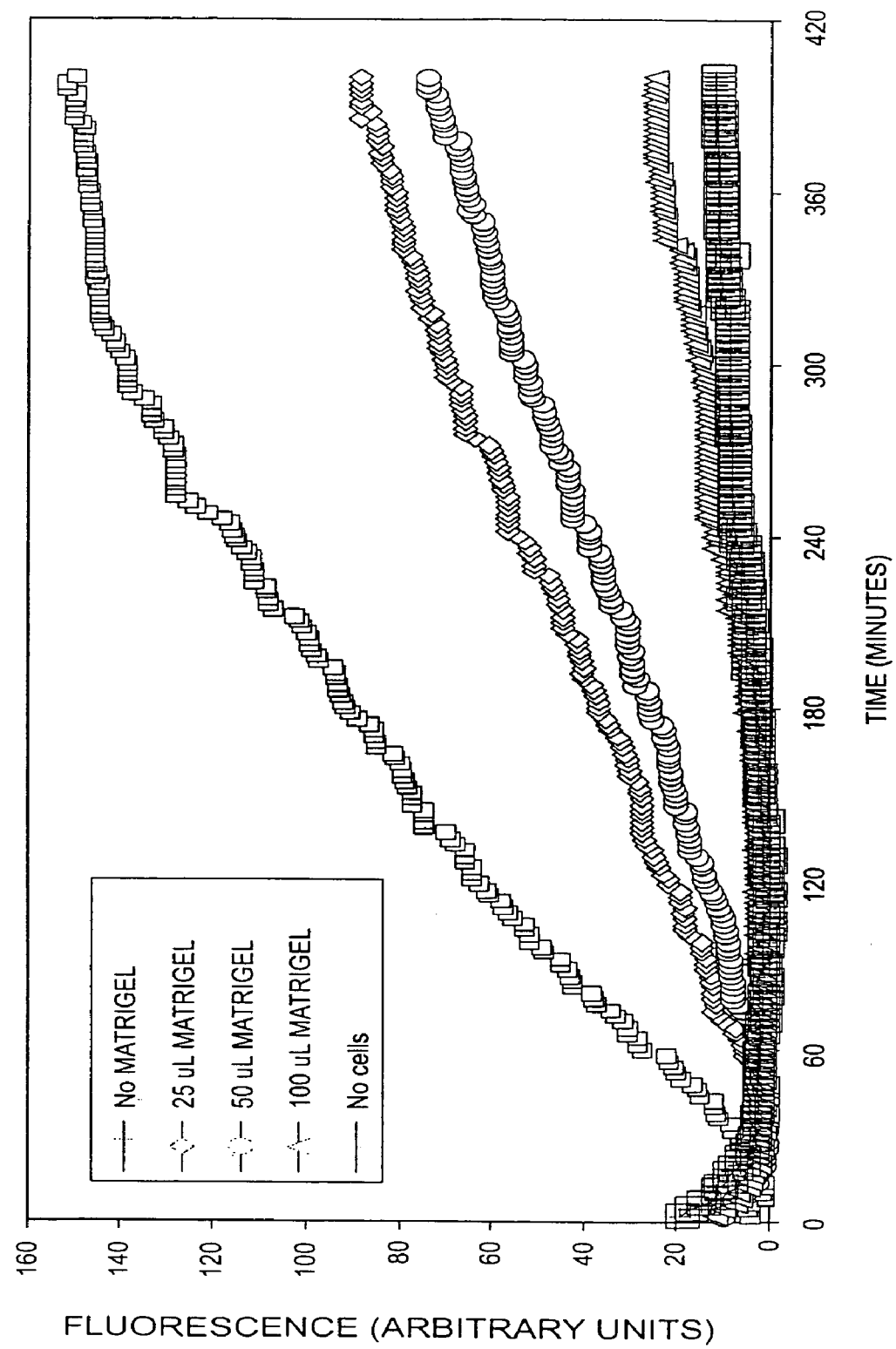
FIG. 17 graphically depicts intensity of fluorescence by plotting fluorescence vs. time for oxygen sensor plates in which MCD-1 cells were grown on the indicated amounts of MATRIGEL®.
Figure 18A:
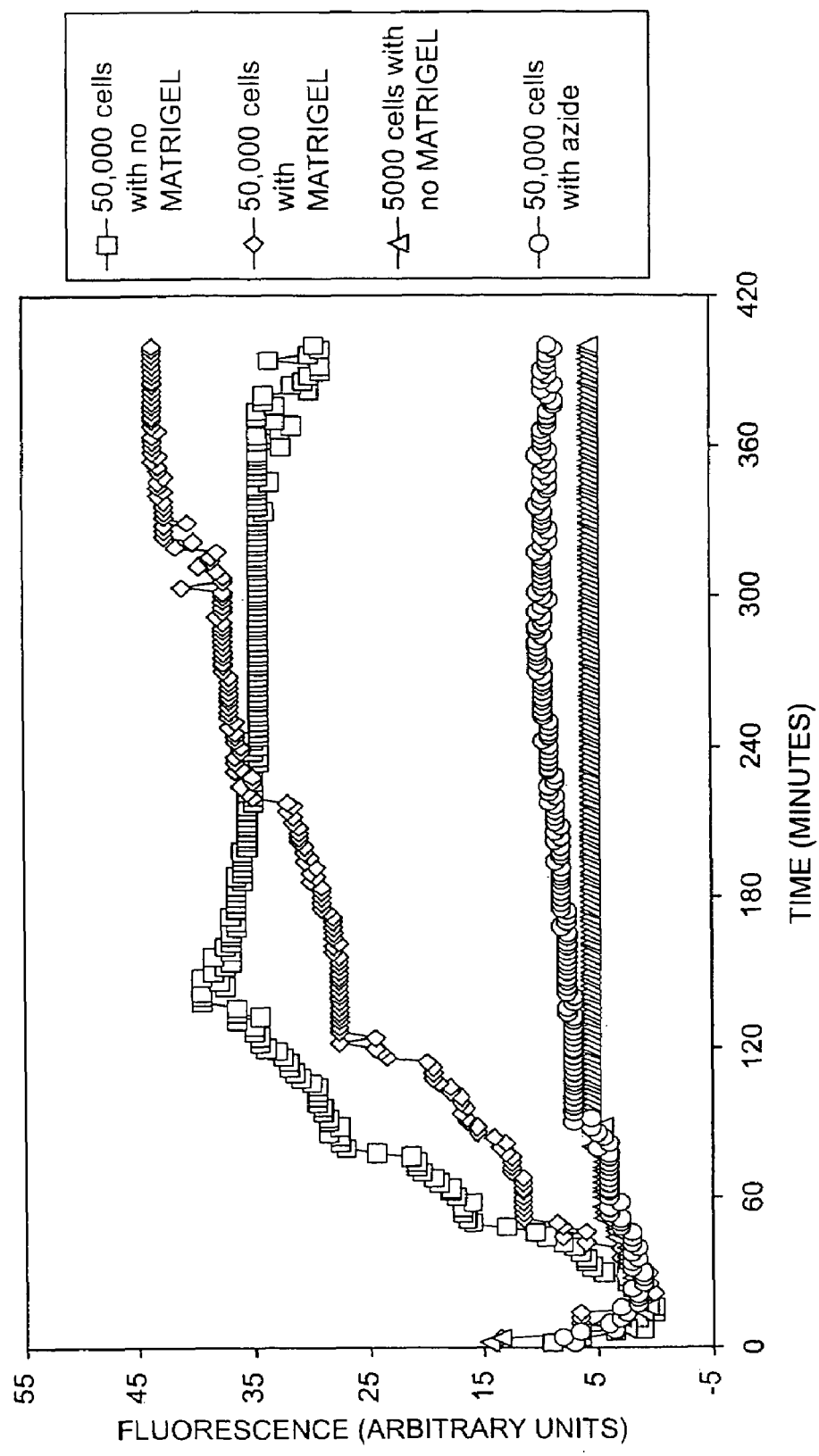
FIGS. 18A, 18B and 18C graphically depict intensity of fluorescence by plotting fluorescence vs. time for oxygen sensor plates in which MCD-1, SK-N-SH, and NIH3T3 cell lines were grown on MATRIGEL®.
Figure 18B:
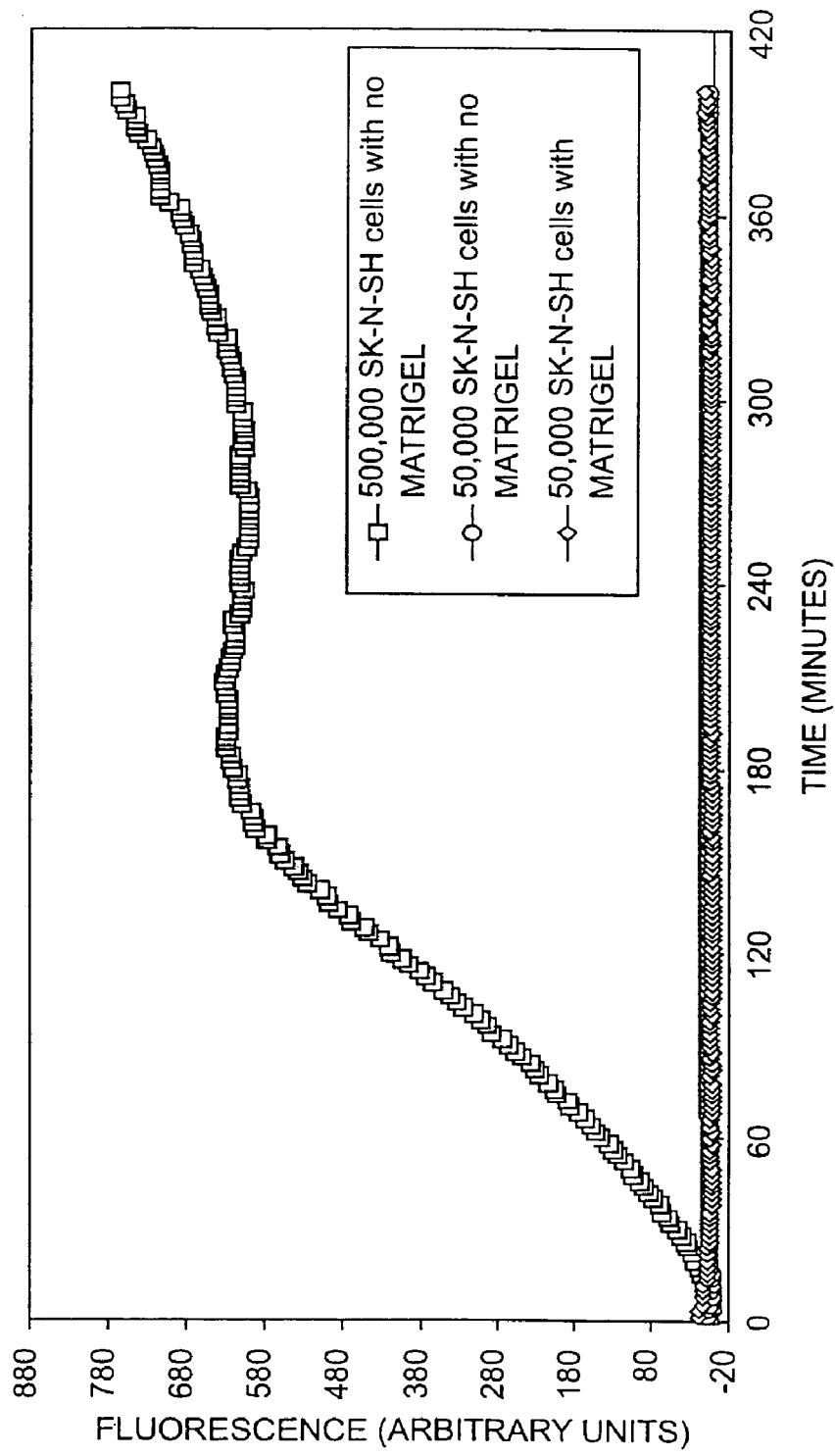

Another feature of these sensor plates is that they may be combined with additional biomaterials such as extracellular matrices. Assays using the matrix MATRIGEL® with various cell lines are shown in FIGS. 17-18. These suggest the oxygen sensor plates may be combined with extracellular matrices to gain information on both oxygen consumption and cellular migration through the extracellular matrix.

A number of cell lines have been tested in the oxygen sensor plates under various conditions as indicated in Table 11 demonstrating the broad applicability of this method to mammalian cell monitoring.

Although the described plates use the luminescent dye 4,7-diphenyl-1,10-phenanthroline ruthenium (II) chloride, other luminescent dyes which exhibit significant oxygen quenching such as tris-2,2'-bipyridyl ruthenium chloride may also be used. A wide variety of silicone rubber polymers and other oxygen permeable polymers may be used to construct the sensors. Sensors may be constructed from sol-gel films ["Tailoring of Sol-Gel Films for Optical Sensing of Oxygen in Gas and Aqueous Phase", C. McDonaugh, B. D. MacCraith, and A. K. McElvoy, Anal. Chem. (1998), vol. 70, 45-50]. Alternatively, useful oxygen sensors can be constructed with the dye covalently immobilized to materials such as controlled pore glass ["Oxygen Sensing in Porous Glass with Covalently Bound Luminescent Ru(II) Complexes", M. P. Xavier, et al, Anal. Chem. (1998), vol. 70, 5184-5189]. Other formats may include adding the sensor to unmodified plates in the form of beads or prongs [see U.S. Pat. No. 5,567,598].

wavelength, 550 nm cut-on filter in the emission window, 10 nm excitation slit, and a 5 nm emission slit. The results are presented in Table 1.

TABLE 1

Fluorescence of Tray Equilibrated with Various Oxygen Gas Levels

| Tray | Average Reading | % Oxygen in Mixture (balance Nitrogen) |
| --- | --- | --- |
| 1 | 803 | 0.00 |
| 2 | 759 | 0.28 |
| 3 | 738 | 0.53 |
| 4 | 524 | 2.45 |
| 5 | 484 | 3.40 |
| 6 | 445 | 5.35 |
| 7 | 208 | 20.90 |

As shown, it can be observed that indicators in wells equilibrated in atmospheric air (Tray 7) displayed a much lower fluorescent signal than wells equilibrated with gas mixtures containing lower concentrations of oxygen (Trays 1-6). This indicates that the fluorescent emission of the fluorescent indicator compound. embedded in the silicone rubber is related to oxygen concentration and that the system can be easily equilibrated with changing oxygen levels. The system allowed 96 sample wells (containing 0.1-0.3 ml sample) to be contained in a single unit that is easily manipulated.

EXAMPLE 2

Use of Indicator System to Measure Relative $O_2$ Concentration Produced by a Reducing Agent The $O_2$ concentration in wells of an Indicator Microtiter tray produced as in Example 1 was varied by the addition of a strong reducing agent, sodium sulfite (which reduces $O_2$ content). A 150 microliter aliquot of the reducing agent (at concentrations ranging from 0 to 1083 parts per million (ppm) sulfite ion in water) was pipetted into wells of the tray. Each well was allowed to react for 30 minutes, open to the atmosphere, and the fluorescence of the indicators measured in a Fluoroskan II Fluorometer (Flow Laboratories, McLean, Va.), having an excitation bandpass filter at a wavelength of 460 nm and an emission cut-on filter at 570 nm. The results are presented in Table 2.

TABLE 2

Effect of Sodium Sulfite on Fluorescence

| ppm sulfite ion | Fluorescence Intensity* |
| --- | --- |
| 0 | 3090 |
| 65 | 3513 |
| 163 | 3545 |
| 325 | 4033 |
| 542 | 11571 |
| 1083 | 11863 |

*Mean of 4 wells

As shown, the wells containing the highest concentrations of reducing agent (and, consequently, the lowest $O_2$ concentration) have the highest fluorescence intensity, thus demonstrating the relationship between $O_2$ concentration and fluorescence.

EXAMPLE 3

Use of Indicator System to Determine the Presence of a Microorganism

A 0.5 McFarland suspension of *E. coli* (ATCC #25922), containing about $1.5 \times 10^8$ CFU/ml, was prepared using an A-Just nephelometer (Abbott Labs, Chicago, Ill.). The suspension was diluted to about $1 \times 10^7$ CFU/ml in Broth A (see Example 1). A 150 microliter aliquot of this suspension was placed into indicator tray wells prepared as in Example 1, and subsequently incubated at 37° C. At intervals, the fluorescence was measured in a Fluoroskan II fluorometer over the period of 1-3½ hours. An increased fluorescence signal was observed over time as shown in FIG. 1. The fluorescence signal from wells containing no organisms showed very little change. The wells containing organisms were significantly brighter when visually observed under a UV light source. Thus, it appears that the metabolic activity of the organisms in the wells caused the fluorescence signal to increase (presumably by decreasing the $O_2$ concentration).

EXAMPLE 4

Dependence of Fluorescence Change on Organism Concentration

A 0.5 McFarland suspension of *E. coli* (ATCC #29522) in sterile trypticase soy broth (TSB, BBL #11768) was made using an A-Just nephelometer (Abbott Labs, Chicago, Ill.).

Figure 2:
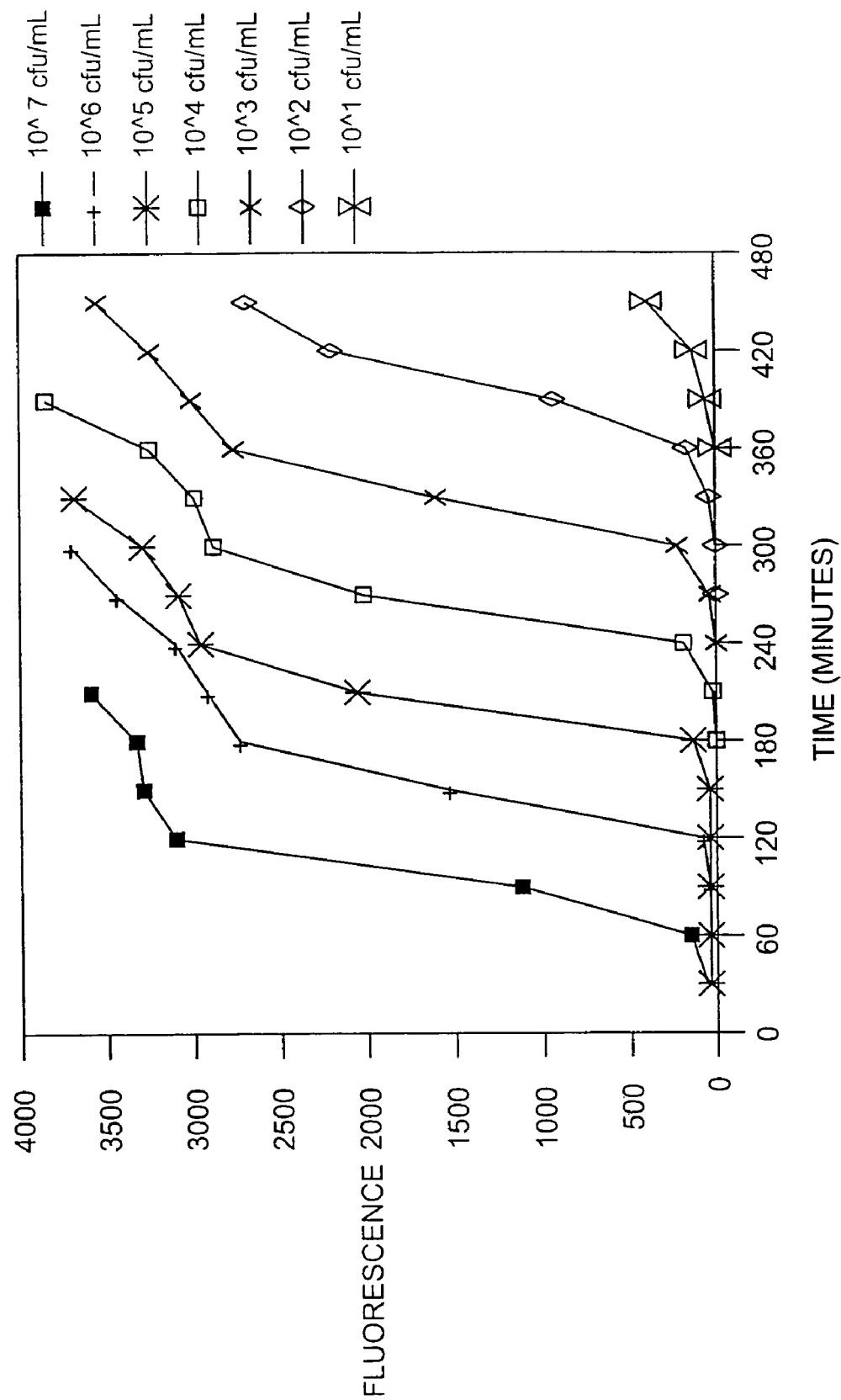
FIG. 2 graphically depicts the intensity of fluorescence as a function of time for indicators in contact with broth inoculated with different concentrations of microorganisms.

A series of E. coli suspensions ranging from 1×10⁷ CFU/ml to about 10 CFR/ml were made by making serial dilutions. A 200 microliter aliquot of each suspension was placed into 8 wells of an indicator tray prepared as in Example 1. The tray was then incubated at 37° C. and the fluorescence measured every 30 minutes in a Fluoroskan II fluorometer. The fluorescence of the 8 wells were averaged and corrected by subtracting the background fluorescence of a sterile TSB well. The change in fluorescence over time is shown in FIG. 2.

As shown, a change in the starting concentration of the organism by a factor of 10 (one log unit) caused a delay of about 1 hour for the fluorescence in the well to exceed 2000 fluorescence units. It is postulated that this delay is due in part to the fact that the system is open to the atmosphere. Oxygen in the air can and does freely diffuse into the medium in an attempt to replace that consumed by the microorganisms. It is further postulated that only when the organisms are present in or have multiplied to sufficient numbers and are metabolically active enough to consume oxygen at a rate approximating or faster than the rate at which oxygen diffuses into the test solution, will the fluorescent signal generated by the indicator element in the bottom of the reservoir show an increase.

EXAMPLE 5

Preparation of an Indicator Microtitration Tray with an Alternate Fluorescent Indicating Molecule A 96 well Microtiter tray was produced essentially as in Example 1, except that tris-(2,2' bipyridyl)-ruthenium (II) chloride hexahydrate (Aldrich Chemical Company, Milwaukee, Wis.) [Ru(BiPy)$_3$Cl$_2$] was substituted for Ru(DPP)$_3$Cl$_2$ in the silicone mixture. A second tray containing 9,10-diphenyl anthracene (DPA) was also prepared. All wells were charged with 150 ul of 1×10⁷ CFU/ml E. coli (ATCC #25922) in broth. Table 3 lists the results at 0, 1, 2, 3, and 4 hours after addition of organisms.

TABLE 3

Fluorescence Counts for Devices with Different Fluorophores

| Fluorescent Compound | Silicone | 0 hr. | 1 hr. | 2 hr. | 3 hr. | 4 hr. |
|---|---|---|---|---|---|---|
| Ru(DPP)$_3$Cl$_2$ (Ex. 3) | A | 2300 | 2315 | 2560 | 8329 | 9000 |
| Ru(BiPy)$_3$Cl$_2$ (Ex. 5) | A | 2866 | — | 3449 | 3951 | 4109 |
| DPA (Ex. 5) | A | 1300 | — | 1385 | 1456 | 1572 |
| Ru(DPP)$_3$Cl$_2$ (Ex. 6) | B | — | 995 | 4334 | 3775 | 3508 |

A = Dow-Corning 3-5024 water-based silicone
B = Wacker white SWS-960 + silicone

As shown, both fluorescent sensor compounds exhibited large increases with fluorescence over time, indicating their suitability for use in this system.

EXAMPLE 6

Preparation of an Indicator Microtitration Tray Using an Alternative Silicone

To demonstrate that the fluorophore can function when embedded in a different matrix, a 96 well Microtiter tray was produced essentially as in Example 1. In this experiment, 10 ul of white SWS-960 RTV silicone (Wacker Silicones, Adrian, Mich.) containing 10 milligrams of Ru(DPP)$_3$Cl$_2$ per liter was dispensed into each well of the tray and allowed to cure. No wash steps were performed on the resultant tray.

The results are presented in Table 3. As in Example 1, wells containing 150 ul of 1×10⁷ CFU/ml E. coli (ATCC #25922) in broth had a much greater fluorescent intensity after several hours at 370 Centigrade.

EXAMPLE 7

Effect of Toxic Substances on the Oxygen Consumption of Microorganisms

Figure 3:
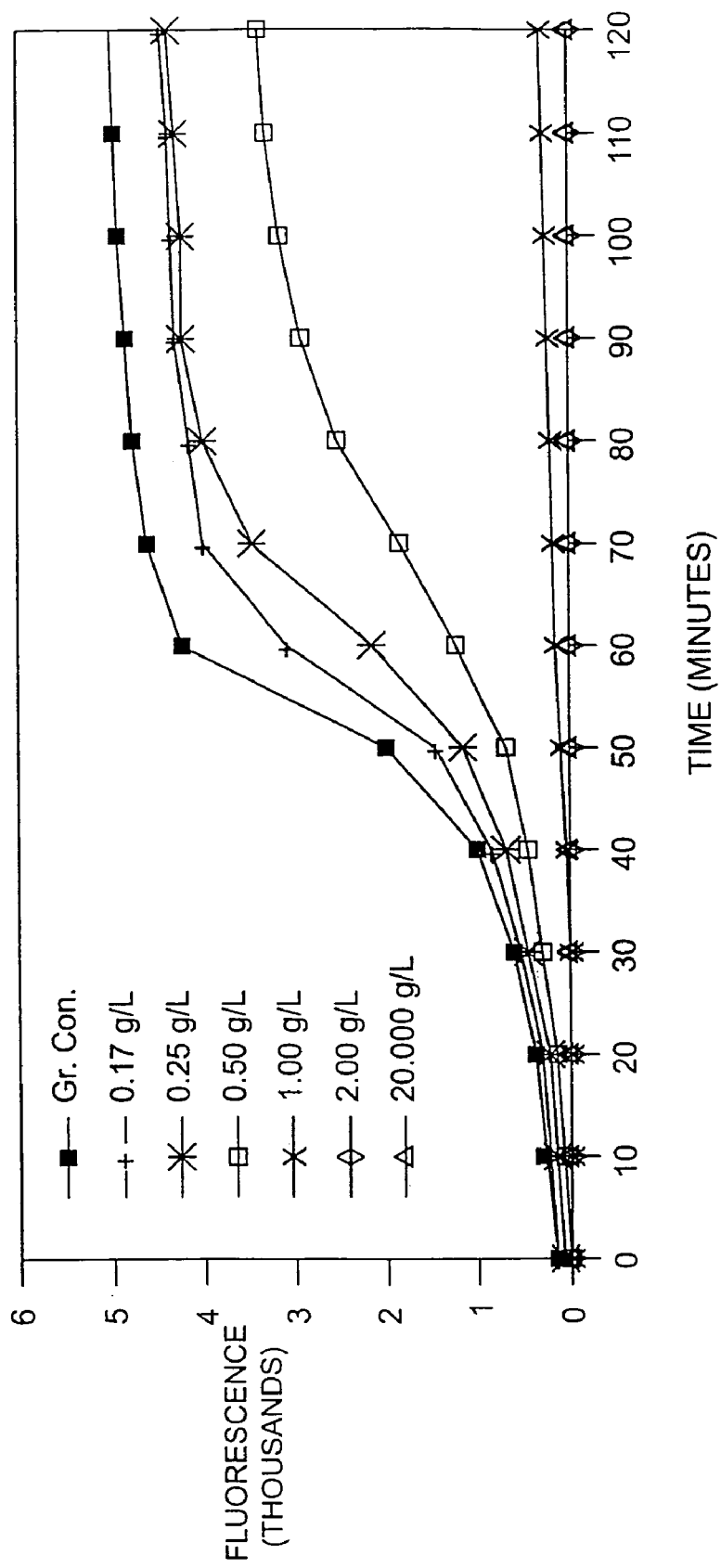
FIG. 3 graphically depicts the intensity of fluorescence as a function of time for indicators in contact with broth inoculated with the same number of organisms but containing different concentrations of phenol.
Figure 4:
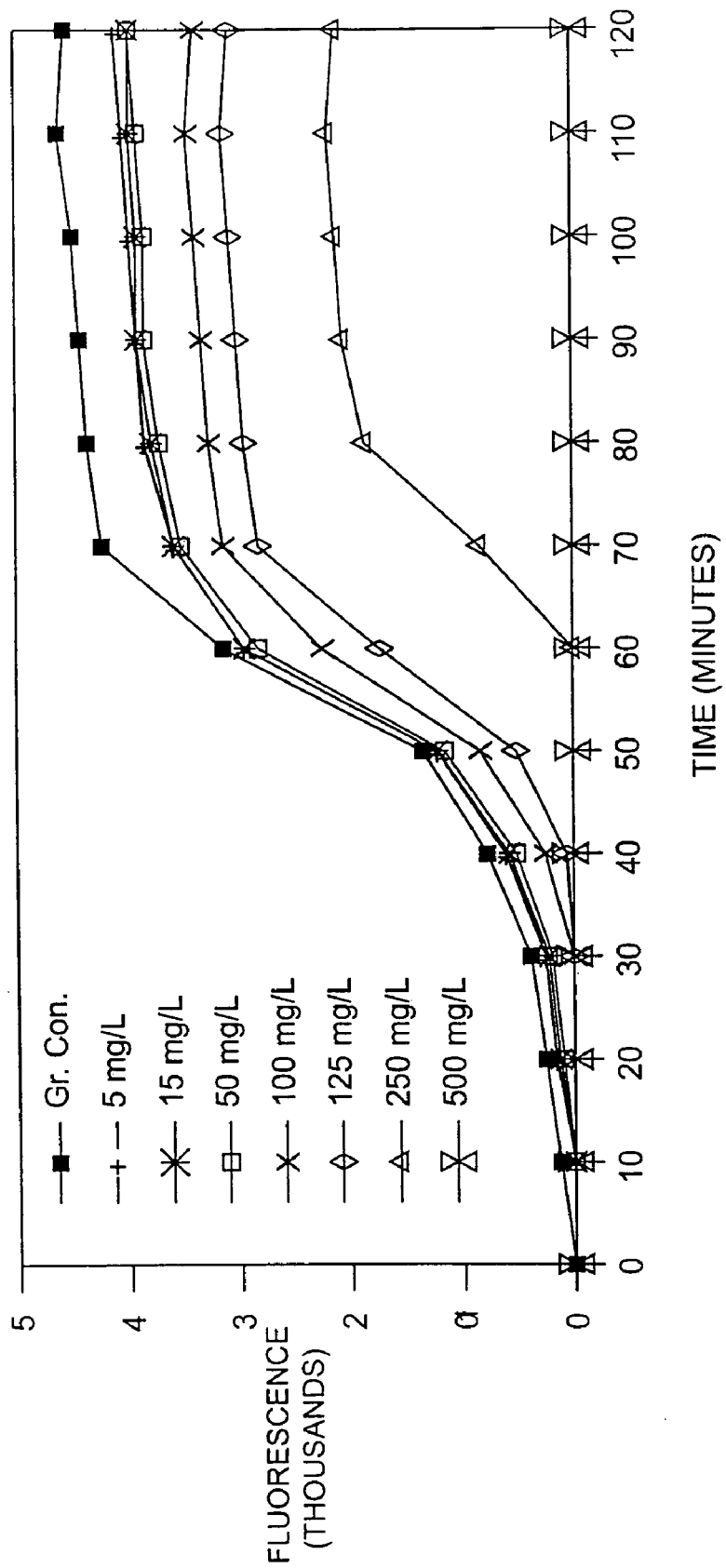
FIG. 4 graphically depicts the intensity of fluorescence as a function of time for indicators in contact with broth inoculated with the same number of organisms but containing different amounts of copper sulfate.

A suspension containing about 3×10⁸ CFU/ml, of Pseudomonas aeruginosa (ATCC #10145) in Broth A was prepared using an A-Just nephelometer. A total of 150 ul of the suspension was placed in each well of the indicator trays prepared as in Example 1; these suspensions were then diluted with solutions of phenol or copper sulfate (which are deleterious to microbial growth) to a final concentration of 1.5×10⁸ CFU/ml. The trays were incubated at 37° C. and their fluorescence measured in a Fluoroskan II at 10 minute intervals. FIGS. 3 and 4 show the effect of phenol and copper sulfate on the response of the system.

As shown, at high levels of additives, growth was suppressed and the fluorescence did not increase with time. Wells containing phenol at 1 gram/liter or more, and copper sulfate at greater than 500 mg/liter, had no increase in fluorescence signal at times less than two hours, indicating absence of actively metabolizing organisms. Thus, measurement of oxygen consumption can be used to probe the metabolism of the organisms.

EXAMPLE 8

Effect of Antibiotics on E. coli

A 0.5 McFarland suspension of E. coli (ATCC #25922) in Broth A (see Example 1) was prepared using an A-Just nephelometer. The suspension was diluted to 1×10⁷ CFU/ml in wells of an indicator tray prepared as in Example 1 containing the antibiotics ciprofloxacin, cefoxitin and cefuroxime at final concentrations of 0.5 to 8 ug/ml. The trays were incubated at 37° C. for 4 hours and their fluorescence measured in a Fluoroskan II fluorometer. The results are presented in Table 4.

TABLE 4

Fluorescence from an Indicator Tray Containing E. coli and Antibiotics
Relative Fluorescence at 4 hrs.

| | Antibiotic | | |
|---|---|---|---|
| Concentration (ug/mL) | Ciprofloxacin | Cefuroxime | Cefoxitin |
| 0.5 | 2537 | 7902 | 8181 |
| 1 | 2621 | 7983 | 8270 |
| 2 | 2461 | 7161 | 7120 |
| 4 | 2527 | 7598 | 3692 |
| 8 | 2424 | 6469 | 2974 |

As shown at all concentrations, the E. coli was sensitive to ciprofloxacin and low fluorescence counts were observed. The E. coli was resistant to the concentrations of cefuroxime and high fluorescence counts were observed. The E. coli was resistant to the 0.5, 1, and 2 ug/ml concentrations of cefoxitin and high counts were observed, but it was sensitive to the higher concentrations of cefoxitin and low counts were observed for 4 and 8 ug/ml. Thus, there is a correlation between the fluorescence and antibiotic concentration, demonstrating that the system of this invention can be used to assess the effects of antimicrobics and to determine the minimum effective concentration compositions.

EXAMPLE 9

Effect of Antibiotics on the Oxygen Consumption of E. coli with $Ru(BiPy)_3Cl_2$ Fluorescence Indicator A 0.5 McFarland suspension of E. coli (ATCC #25922) in Broth A (see Example 1) was prepared using an A-Just nephelometer. The suspension was diluted to $1\times10^7$ CFU/ml in wells of an indicator tray prepared as in Example 5 ($Ru(BiPy)_3Cl_2$ indicator) containing the antibiotics ciprofloxacin, cefoxitin and cefuroxime at final concentrations of 0.5 to 8 ug/ml. The trays were incubated at 37° C. for 4 hours and their fluorescence measured in a Fluoroskan II fluorometer. The results are listed in Table 5.

TABLE 5

Fluorescence from an Indicator Tray Containing E. coli and Antibiotics
Relative Fluorescence at 4 hrs.

| | Antibiotic | | |
|---|---|---|---|
| Concentration (ug/mL) | Ciprofloxacin | Cefuroxime | Cefoxitin |
| 0.5 | 507 | 1155 | 1171 |
| 1 | 428 | 1539 | 1491 |
| 2 | 308 | 1183 | 1338 |
| 4 | 403 | 1170 | 832 |
| 8 | 323 | 1194 | 559 |

As shown, as in Example 8, at these concentrations the E. coli is sensitive to ciprofloxacin and low fluorescence counts were observed. The E. coli is resistant to these concentrations of cefuroxime and high fluorescence counts were observed. The E. coli is resistant to the 0.5, 1, and 2 ug/ml concentrations of cefoxitin, high counts were observed; it was sensitive to higher concentrations of cefoxitin and lower counts were observed for 4 and 8 ug/ml. Thus, the results indicated that $Ru(BiPy)_3Cl_2$ can also be used in a fluorescence indicator.

EXAMPLE 10

Effect of Antibiotics on the Oxygen Consumption of Microorganisms Using DPA Fluorescence Indicator A 0.5 McFarland suspension of E. coli (ATCC #25922) in Broth A was prepared using an A-Just nephelometer. The suspension was diluted to $1\times10^7$ CFU/ml in wells of an indicator tray prepared as in Example 5 (DPA indicator) containing the antibiotics ciprofloxacin, cefoxitin and cefuroxime at final concentrations of 0.5 to 8 ug/ml. The trays were incubated at 37° C. for 4 hours and their fluorescence measured in a Fluoroskan II. The results are presented in Table 6.

TABLE 6

Fluorescence from an Indicator Tray Containing E. coli and Antibiotics
Relative Fluorescence at 4 hrs.

| | Antibiotic | | |
|---|---|---|---|
| Concentration (ug/mL) | Ciprofloxacin | Cefuroxime | Cefoxitin |
| 0.5 | 91 | 183 | 192 |
| 1 | 109 | 197 | 173 |
| 2 | 94 | 195 | 164 |
| 4 | 74 | 160 | 101 |
| 8 | 68 | 161 | 95 |

As shown, at these concentrations the E. coli is sensitive to ciprofloxacin and low fluorescence counts were observed. The E. coli is resistant to these concentrations of cefuroxime and high fluorescence counts were observed. The E. coli is resistant to the 0.5, 1, 2 ug/ml concentration of cefoxitin, high counts were observed; it was sensitive to higher concentrations and lower counts were observed for 4 and 8 ug/ml as in Examples 8 and 9, indicating that DPA is also useful as a fluorescence indicator.

EXAMPLE 11

Effect of Open and Closed Systems on Oxygen Measurements

Figure 5A:
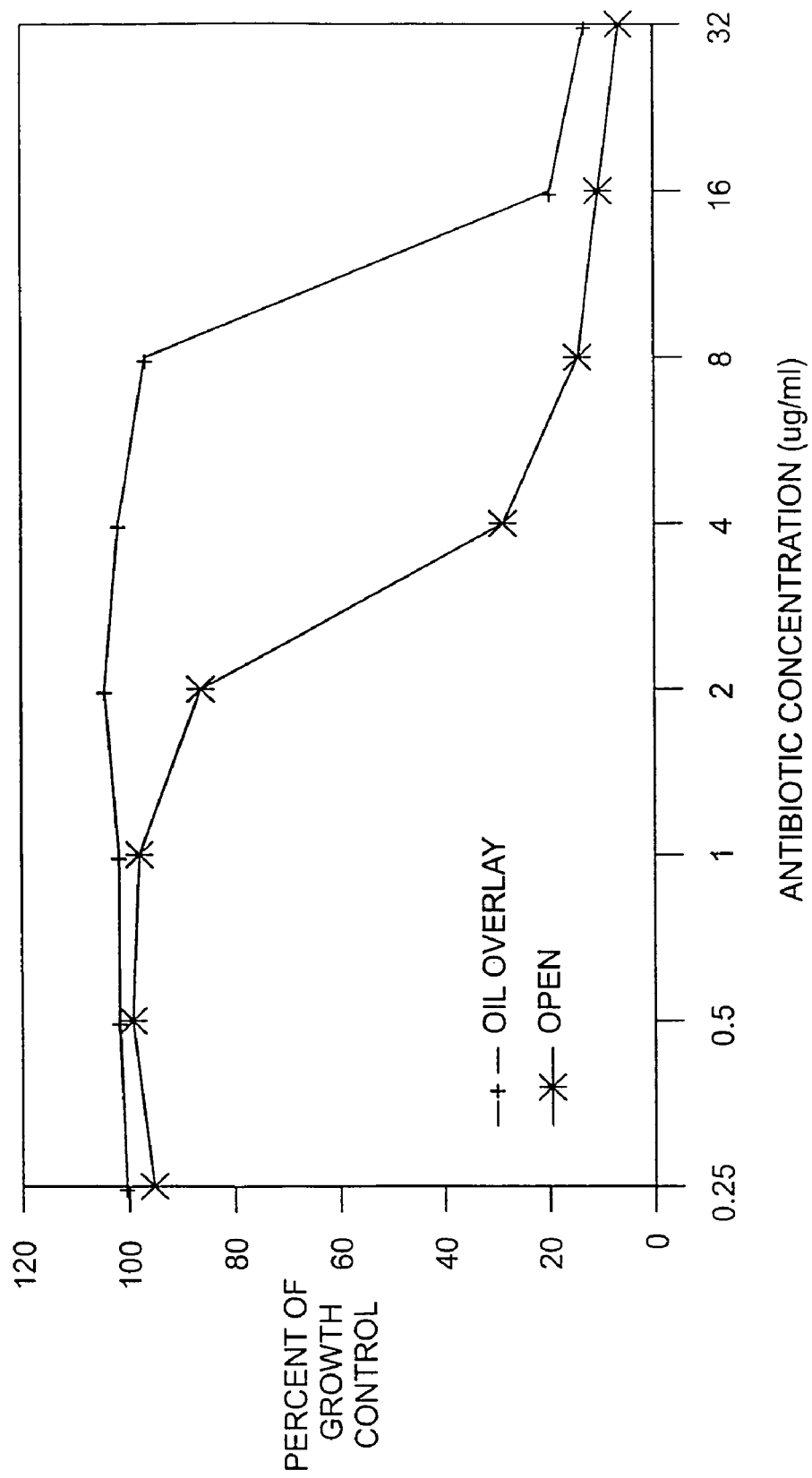
FIG. 5A graphically depicts the fluorescence, as a function of indicators in contact with broth inoculated with the same concentration of microorganisms but different concentrations of cefuroxime. Some wells were covered with mineral oil to prevent oxygen from diffusing into the wells. The fluorescence is given as a percent of growth control.
Figure 5B:
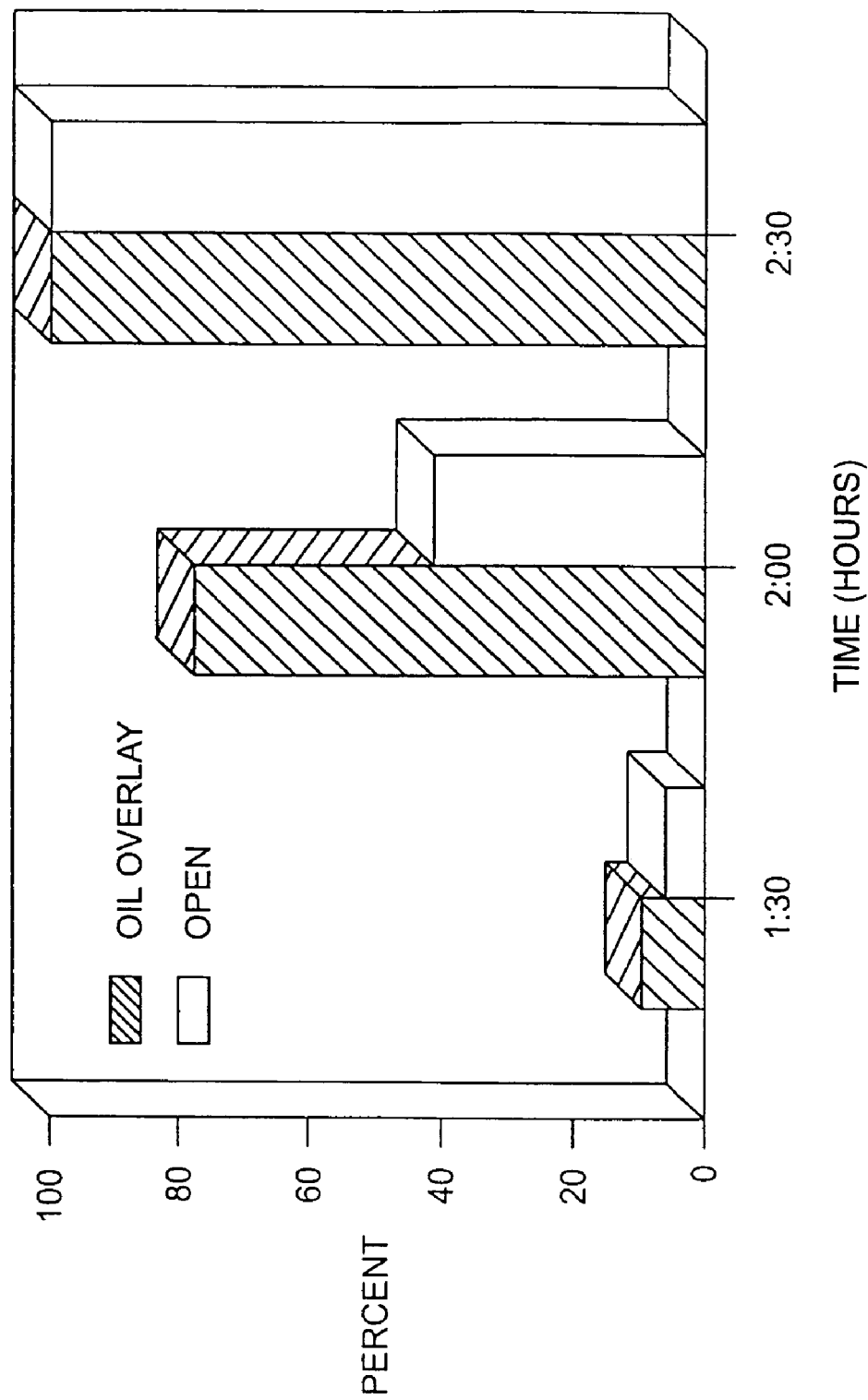
FIG. 5B graphically depicts the fluorescence as a percent of the growth control in wells that are overlaid with oil or left open and measured at several different times.

A 96 well indicator microtiter tray was produced substantially as in Example 1. Duplicate wells in the tray were supplemented with the antibiotic cefuroxime in the concentration range of 0.25 to 32 ug/ml. One hundred and fifty microliters of a suspension of E. coli (ATCC #11775) was added to the wells to yield about $3\times10^7$ CFU/ml. One of each duplicate well was overlaid with mineral oil to inhibit diffusion of oxygen into the wells, the other duplicate was left open to the air. The tray was incubated at 37° C. for 5 hours, the fluorescence was measured in a Fluoroskan II fluorometer and that fluorescence was compared with the average of several wells containing no antibiotic to yield a percent of the growth control at each antibiotic concentration. FIG. 5A shows the behavior of the open and covered wells at five hours as a function of cefuroxime concentration. FIG. 5B shows the change in fluorescence of the growth control wells when open or overlaid with mineral oil.

The "closed system" overlaid with mineral oil did not show an effect on oxygen consumption by the 4 and 8 ug/ml concentrations of antibiotic while those wells with no mineral oil showed correctly that this organism is sensitive to cefuroxime at these concentrations. This difference is due, presumably to the time lag needed for the antibiotic to affect the organism; it is believed that during this time the oxygen is brought to an artificially low level by the ongoing metabolic activity of the organisms.

Thus, to utilize the invention with optimum sensitivity for the detection of the effect of toxins on organisms, the sample reservoir permits the influx of oxygen.

EXAMPLE 12

The Effect of Sample Volume on Indicator Trays

A 0.5 McFarland suspension of E. coli (BDMS Culture collection #7133) was diluted to $1\times10^7$ CFU/ml in Broth A. Different volumes (from 10 ul to 300 ul) of the diluted suspension were placed into wells of an indicator tray produced as in Example 1. The tray was incubated at 37° C. and the fluorescence measured in a Fluoroskan II at 30 minute intervals. Fluorescence from the same volume of sterile broth was subtracted to give the fluorescence change cause by the microorganism. The results are presented in Table 7.

TABLE 7

Effect of Sample Volume on Indicator Tray Fluorescence
Relative Fluorescence

| Sample Volume (ul) | 0 hr. | 1 hr. | 2 hr. | 2.5 hr. | 3 hr. | 3.5 hr. | 4 hr. |
|---|---|---|---|---|---|---|---|
| 10 | 0 | 0 | 0 | 0 | 0 | 4 | 139 |
| 20 | 0 | 0 | 275 | 795 | 814 | 1218 | 1958 |
| 40 | 0 | 245 | 683 | 1883 | 2108 | 2613 | 3240 |
| 60 | 0 | 80 | 1559 | 3497 | 4847 | 6226 | 6827 |
| 80 | 0 | 82 | 1798 | 5340 | 8333 | 8810 | 8801 |
| 100 | 0 | 31 | 1848 | 5952 | 7672 | 7962 | 7961 |
| 125 | 0 | 103 | 2798 | 6286 | 7580 | 7852 | 7852 |
| 150 | 0 | 32 | 2539 | 6005 | 6568 | 6759 | 6886 |
| 175 | 0 | 51 | 2574 | 6149 | 6993 | 6987 | 6798 |
| 200 | 0 | 59 | 2376 | 5355 | 5742 | 5944 | 5826 |
| 250 | 0 | 115 | 2172 | 5373 | 5695 | 5822 | 5759 |
| 300 | 0 | 107 | 2538 | 4650 | 4727 | 4825 | 4778 |

Briefly, it was observed that those wells with 40 ul or less of sample showed less that ½ rease in relative signal observed in wells with 80 ul or more at times of 2 hours or more. It is believed that in the wells containing 40 ul or less, too little volume was present for the organisms to effectively consume oxygen faster than it could diffuse into the small volumes of sample.

EXAMPLE 13

Use of Indicator System Without a Fluorometer

Indicator trays were prepared using the same fluorescent compound and silicone as in Example 1. However, the trays were made of clear plastic and the wells had round bottoms (#4-3918-2, BD Labware, Lincoln Park, N.J.). Two nanograms of $Ru(DPP)_3Cl_2$ in 10 ul of silicone were placed in each well of the tray and no wash steps were performed. Samples of *Ps. aeruginosa* (BDMS Culture collection #N111) and *E. coli* (ATCC #25922) were diluted to Broth A (see Example 1) $1\times10^7$ CFU/ml in Broth A containing either 0 to 32 ug/ml cefuroxime, 0.12 to 8 ug/ml ciprofloxacin or 0 to 32 ug/ml cefoxitin and charged to the trays. The trays were incubated for 4 hours at 37° C. and subsequently placed on the stage of an ultraviolet transilluminator (#TX-365A, Spectronics Corp., Westbury, N.Y.) which served as an excitation source. The resulting fluorescence was observed from directly above the trays at a distance of 1 foot through a 550 cut-on filter (#LL-550-S-K962, Corion, Holliston, Mass.). It was readily observed that wells which contained either no antibiotics or concentrations of antibiotics that did not affect the organisms demonstrated a high level of fluorescence. Wells with either no organisms or higher antibiotic levels had a much lower level of fluorescence. The lowest concentration of antibiotic to significantly lower the fluorescent emissions for each organism is shown in Table 8 along with the MIC concentration determined using an overnight microdilution antimicrobial susceptibility test.

TABLE 8

Fluorescence Results Obtained Without Use of an Instrument MIC

| | Cefuroxime | | Ciprofloxacin | | Cefoxitin | |
|---|---|---|---|---|---|---|
| | Visual | Reference | Visual | Reference | Visual | Reference |
| *Ps. aeruginosa* | >64 | >64 | 1 | 0.5 | >64 | >64 |
| *E. coli* #25922 | 16 | 8 | <0.12 | <0.12 | 8 | 4 |

EXAMPLE 14

Figure 6:
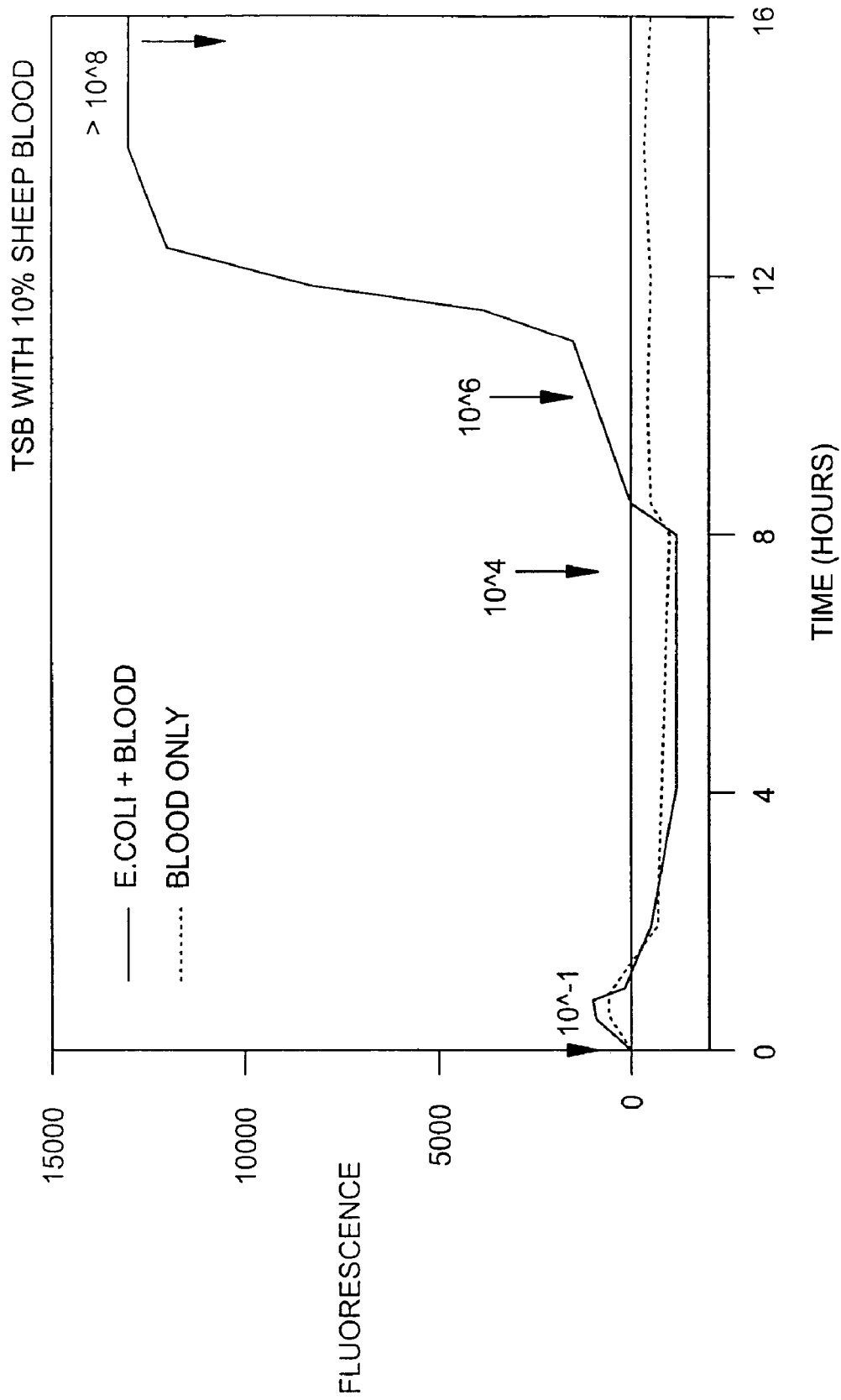
FIG. 6 graphically depicts the intensity of fluorescence of indicators in blood culture bottles when measured continuously over 16 hours. The arrows indicate the times when samples were removed in order to quantify the concentration of organisms present.

Use of Indicator to Detect the Presence of a Low Level of Bacteria In a Medium Containing Blood Tissue culture flasks (Falcon #3084, BD Labware, Lincoln Park N.J.) were prepared with one side coated with 3 mls of Dow Corning Water-based Emulsion containing 68 ng of $Ru(DPP)_3Cl_2$. The flasks were sterilized using ethylene oxide. One hundred thirty five mls of TSB broth (BBL #11768) containing about 0.05 CFU/ml *E. coli* (ATCC #25922) and 15 mls of defibrinated sheep blood was added to one of the flasks. A control flask contained 135 mls of TSB and 15 mls of blood but no organisms. The caps of the flasks were loosened to allow air circulation and the flasks were incubated at 37° C. in an upright position. A fiber optic probe allowed the fluorescence from the flasks to be measured by a Perkin Elmer LS-5B spectrofluorometer located several feet from the incubator. The fluorometer measured the flasks at 485 nm excitation wavelength with a 10 nm slit width and a 550 nm cut-on emission filter. A strip chart was attached to the fluorometer and the fluorescence monitored continuously for 16 hours. At 7.5, 10.5 and 16 hours during the incubation period a 100 ul aliquot was removed from the test flask, diluted 1:100 in sterile TSB and 100 ul of the dilution was spread on each of three TSA plates to determine the number of CFU/ml present in the flask. The results are graphically depicted in FIG. 6.

As shown, the non-invasive techniques of this invention can be used for the detection of organisms in blood, a very critical and demanding task. The flask contained a very cloudy and turbid solution which is continuously monitored for sixteen hours, and measurement of fluorescence showed a direct correlation to the growth of organisms. This growth was readily detected by 11 hours, when the concentration of organisms had just exceeded $10^6$ CFU/ml.

EXAMPLE 15

Indicator Coated on the Spherical Ends of FAST Tray Lid Prongs

This example monitored bacterial respiration with oxygen indicators coated on the spherical ends of FAST tray (Becton Dickinson) lid prongs. Three different indicators were evaluated.

The first indicator prepared was a mixture of 1 ml of 2 mg/ml dichloromethane solution of $Ru(DPP)_3Cl_2$ and 10 ml Dow-Corning 3-5024 water-based silicone emulsion. The spherical ends of FAST tray lid prongs were dipped into a shallow reservoir of the indicator solution, removed, placed prong side down in a rack, and allowed to cure by evaporation. The second indicator was prepared by mixing 3 mL Wacker SWS-960 clear silicone dispersion, 6 mL petroleum ether, and 0.5 mL of the 2 mg/mL dichloromethane solution of $Ru(DPP)_3Cl_2$. The spherical ends of FAST tray lid prongs were coated with this indicator in the same manner as with the first indicator and allowed to cure by evaporation of the solvents and reaction with atmospheric moisture. The third indicator was prepared in the same manner as the second but Wacker SWS-960 white silicone was used.

A $1\times10^7$ CFU/mL suspension of *E. coli* ATCC #25922 in Mueller Hinton broth was prepared; 150 microliter aliquots were pipetted into the odd numbered rows of a microtiter tray, while 150 microliter aliquots of uninoculated Mueller Hinton broth were pipefted into the wells of the even numbered columns. The lids containing the indicator coated prongs were placed on the trays. The lidded trays were placed in a 37° C. high humidity incubator for 3 hours.

Following the three hour incubation, the trays were placed on a transparent glass plate. A mirror was positioned below the glass plate in such a manner that the bottom of the tray was visible in the mirror. A 365 nm ultraviolet source which evenly illuminated the entire tray was positioned about one inch from the top of the tray. A box, with a small window through which the mirror could be seen, was placed over the assembly to block room light, and a 550 nm cut-on filter was placed in the box window. With this assembly the fluorescence from the indicator coated spherical ends of the FAST tray lid prongs could be visualized through the tray bottom. Table 9 contains the results of visual observations of the trays evaluated in this manner.

TABLE 9

Visual Observations of Indicator Coated Lid Prongs Viewed Through Tray Bottoms

| Silicone | Observations |
| --- | --- |
| Dow-Corning | Very bright fluorescence from spheres immersed in organism containing wells. Very weak fluorescence from prongs in uninoculated wells. |
| Wacker Clear | Some visible difference between prongs immersed in inoculated and uninoculated wells. Difference much less observable than with Dow-Corning indicator. |
| Wacker White | Very bright fluorescence from spheres immersed in inoculated wells, intensity about equal to Dow-Corning indicator. Some weak fluorescence from spheres in uninoculated wells. |

Thus, all three indicator systems produced desirable results, with the Dow Corning and Wacker White exhibiting much more distinguishable differences between the inoculated and uninoculated wells.

EXAMPLE 16

Indicators Consisting of $Ru(DPP)_3Cl_2$ Adsorbed on Silica Gel Particles Embedded in UV Cured Silicone Rubber Indicators were prepared by adsorbing $Ru(DPP)_3Cl_2$ onto silica gel particles and embedding these particles into Loctite Nuva-Sil silicone rubbers. A variety of indicators were prepared using silica gel particles of different mesh sizes, different amounts of adsorbed fluorophore, different ratios of silica gel to silicone, and two types of Loctite Nuva-Sil (Nuva-Sil 5091 and Nuva-Sil 5147). Table 10 contains the characteristics of the indicators prepared and the visual results obtained from the

EXAMPLES

The following examples illustrate certain preferred embodiments of the instant invention but are not intended to be illustrative of all embodiments.

EXAMPLE 1

Preparation of an $O_2$-Sensitive Indicator Microtitration Tray

The fluorescent compound tris 4,7-diphenyl-1,10-phenanthroline ruthenium (II) chloride ($Ru(DPP)_3Cl_2$) was synthesized using the procedure of Watts and Crosby (J. Am.Chem. Soc. 93, 3184(1971)). A total of 3.6 mg of the compound was dissolved in 2.0 ml dimethyl sulfoxide (D-5879, Sigma Chemical, St. Louis, Mo.) and the resultant solution was then added slowly, with stirring, to 1300 ml silicone rubber forming solution (Water Based Emulsion #3-5024, Dow Corning, Midland, Mich.). A 35 microliter aliquot of the mixture was subsequently dispensed into each well of a 96 well, flat bottom, white microtiter tray (#011-010-7901, Dynatech, Chantilly, Va.), and the system was subsequently cured overnight in a low humidity (less than 25% RH), 60° C. incubator. After curing, the trays were washed by either soaking or by filling and emptying each well several times with each of the following reagents; a) absolute ethanol, b) 0.1 M phosphate buffer pH 7.2, c) hot distilled water (about 45° C.) and d) ambient temperature distilled water.

Subsequently, 150 microliters of a Broth A, consisting of 35% Mueller Hinton II (BBL #124322, BD Microbiology Systems, Cockeysville Md.), 15% Brucella (BDL #11088), and 50% distilled water, was dispensed into each well of the tray, and the tray was then placed in a glove box containing the desired concentration of oxygen, mixed with nitrogen to obtain a total pressure of 1 atm. The tray was kept in the glove box for at least 24 hours, after which it was covered with an adhesive backed mylar sheet and removed.

The fluorescent emissions of the fluorescent compound in the bottom of each well of the tray were then measured using a Perkin-Elmer LS-5B equipped with a microtiter reader attachment at the following instrument settings: 485 nm excitation indicators in contact with microorganism suspensions. An exemplary procedure used for the preparation of the indicators is presented below.

Ten grams of 100-200 mesh Davisil silica gel (Aldrich, Milwaukee, Wis.) was weighed into a 500 mL round bottom evaporation flask. Forty three milliliters of a 0.14 mg/mL ethanol solution of $Ru(DPP)_3Cl_2$ was pipetted into the flask. The ethanol was removed by rotary vacuum evaporation resulting in the adsorption of the $Ru(DPP)_3Cl_2$ on the silica gel at a concentration of 0.6 mg $Ru(DPP)_3Cl_2$/gm silica gel. Four grams of this silica gel were mixed with 16 g Loctiote Nuva-Sil 5091 (Locite, Newington, Conn.) resulting in a 20% w/w silica/silicone ratio. Twenty-five microliter aliquots of this mixture were pipetted into the wells of a microtiter tray. The silicone was cured by exposure to high intensity ultraviolet radiation for 15 seconds in a Loctite Zeta 7200 UV curing chamber. The other indicators in Table 10 were similarly prepared.

To evaluate the indicators, 150 microliters of a $1\times10^7$ CFU/mL suspension of *E. coli* (ATCC #25922 in Mueller Hinton II broth (BBL) was pipetted into selected wells of the microtiter tray; uninoculated broth was pipetted into other wells. The tray was incubated in a high humidity 35° C. incubator for 3 hours. To visualize the fluorescence from the indicator the tray was placed on the stage of a 365 nm UV transilluminator; the fluorescence from the indicator was observed from above through a 550 nm cut-on filter. A "+" sign in the Response column of Table 10 indicates that a visibly discernible increased fluorescence was observed from the wells containing the organism.

TABLE 10

Indicator Formulations and Responses

| Mesh Size | mg Ru(DPP)$_3$Cl$_2$ /g Silica | Wt % Silica | Silicone | Response |
|---|---|---|---|---|
| 60–100 | 0.2, 0.4, 0.6 | 5, 10, 20 | 5091, 5147 | +* |
| 100–200 | 0.2, 0.4, 0.6 | 5, 10, 20 | 5091, 5147 | +* |
| 200–425 | 0.2, 0.4, 0.6 | 5, 10, 20 | 5091, 5147 | +* |

*Represents result from all 18 trials (9 each for Silicone 5091 and 5147).

In replicate trials utilizing wells with no microorganisms, the indicators displayed little or no light (although at higher (0.6 mg/gm) concentrations of indicator, a dim fluorescence was noted).

EXAMPLE 17

Oxygen Sensor Not In Direct Contact With Sample Fluid

Figure 7:
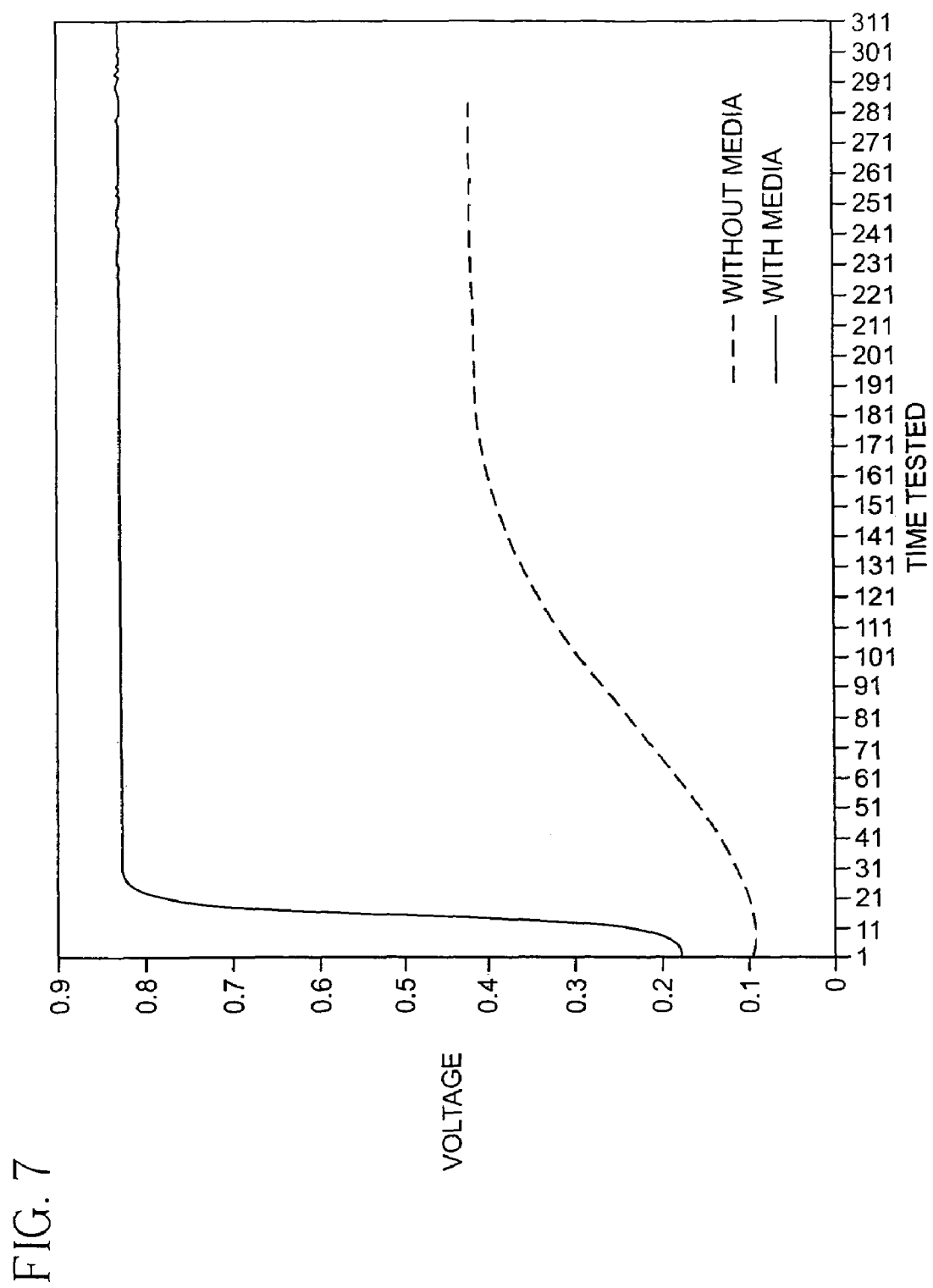
FIG. 7 depicts the data collected in the BACTEC® instrument indicating the change in fluorescence intensity indicative of the growth of *P. aeruginosa*.
Figure 8:
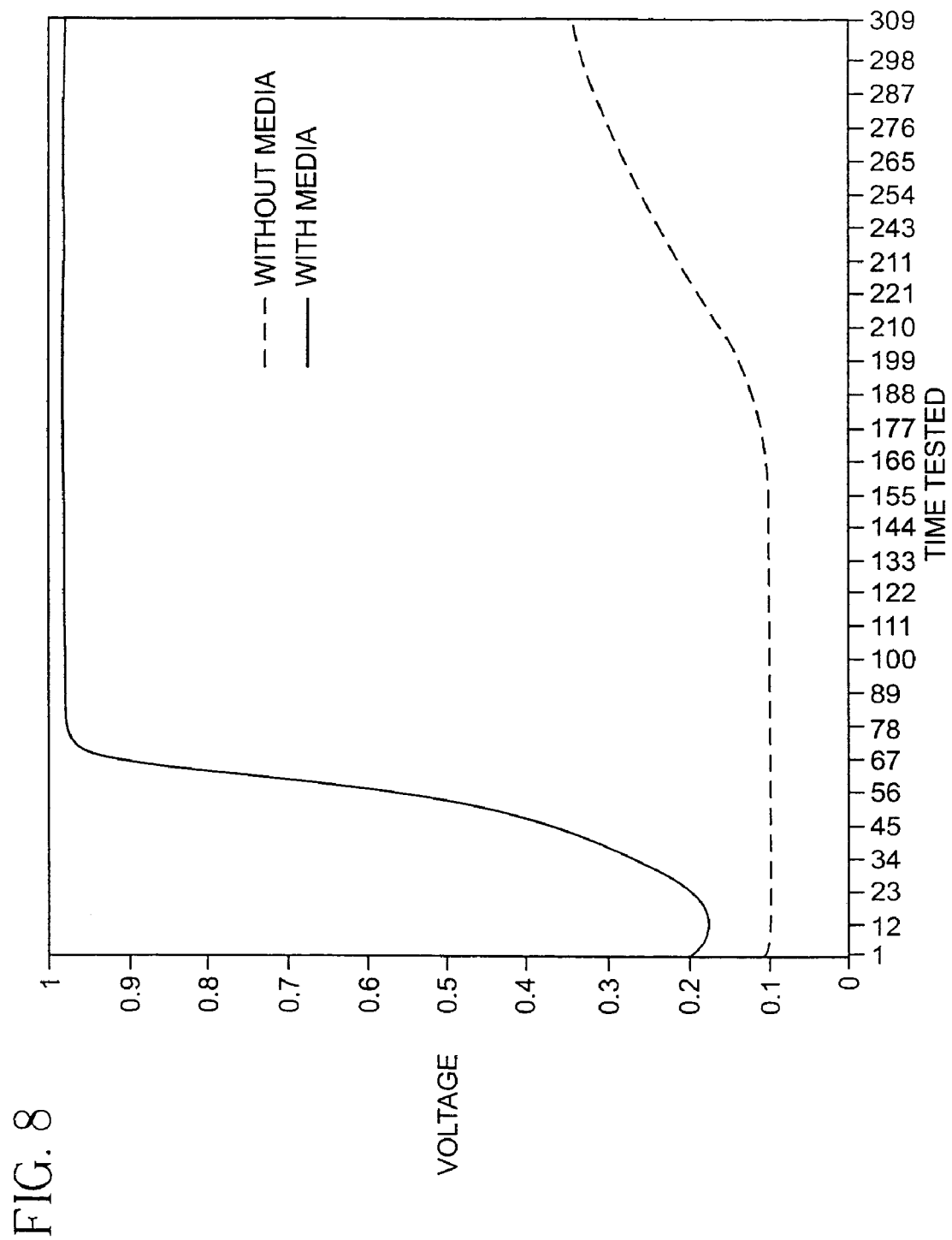
FIG. 8 depicts the data collected in the BACTEC® instrument indicating the change in fluorescence intensity indicative of the growth of *M. fortuitum*.
Figure 9:
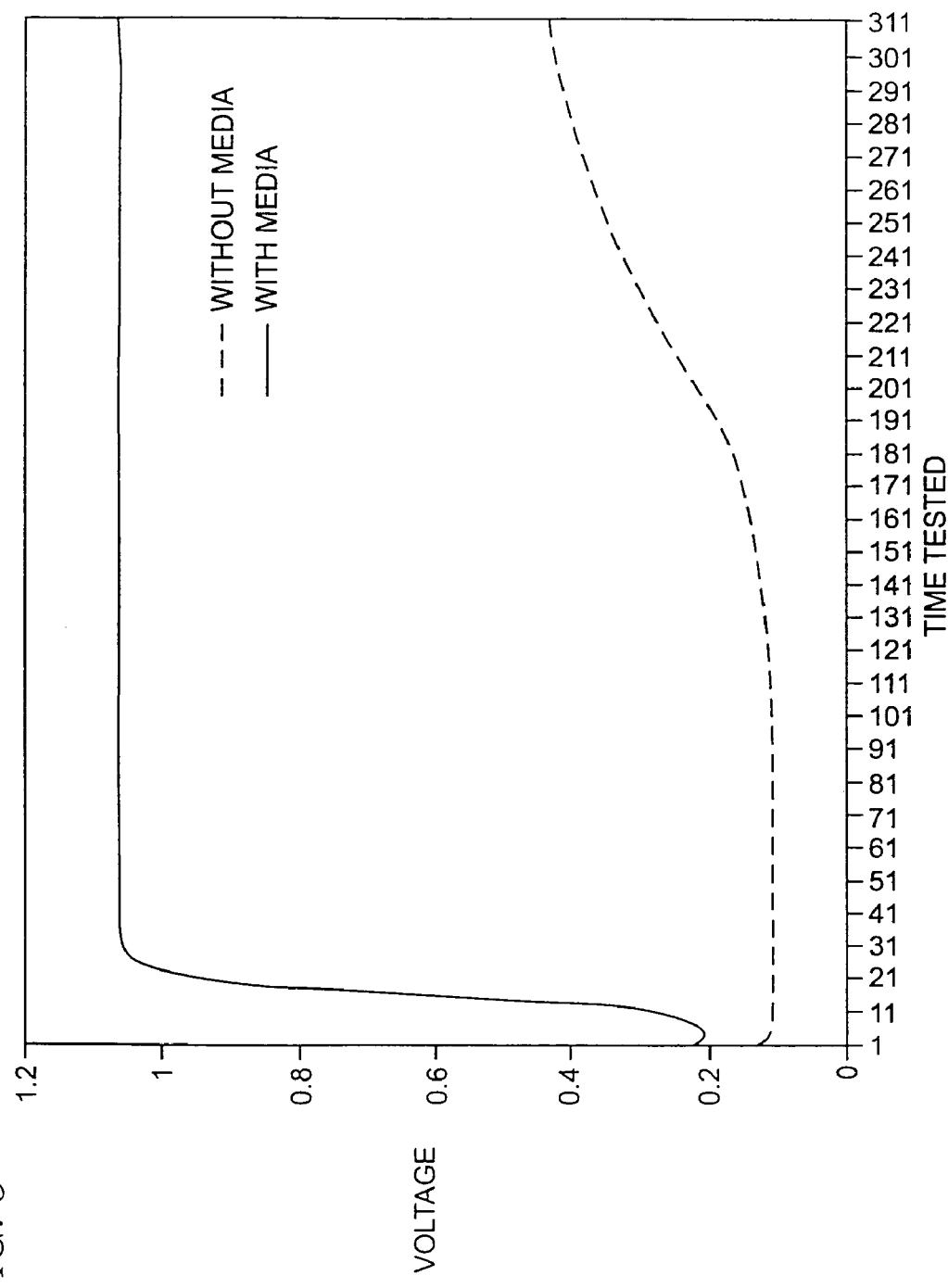
FIG. 9 depicts the data collected in the BACTEC® instrument indicating the change in fluorescence intensity indicative of the growth of *E. coli*.

Test vials (80 mL volume) containing 60 mL of media and oxygen sensor (OS) were inoculated with the following organisms: *Pseudomonas aeruginosa*, *Mycobacterium fortuitum* and *Escherichia coli*. The vials were connected to 80 mL vials without broth with oxygen impermeable rubber tubing. The vials were then entered into adjacent stations in a BACTEC® 9240 instrument. Data was collected on the two vials over a 50 hour period. The results of these tests are presented in FIGS. 7 through 9. FIG. 7 depicts the data collected in the BACTEC® instrument indicating the change in fluorescence intensity indicative of the growth of *P. aeruginosa*. FIG. 8 depicts the data collected in the BACTEC® instrument indicating the change in fluorescence intensity indicative of the growth of *M. fortuitum*. FIG. 9 depicts the data collected in the BACTEC® instrument indicating the change in fluorescence intensity indicative of the growth of *E. coli*. For each of the figures the bold line in these figures represent the data collected in the vials containing broth; the light lines represent the data collected by the sensor that is not in direct contact with the liquid broth. In all three cases, oxygen consumption was observed in the vials without broth. The pattern of oxygen consumption exhibited in these vials indicates logarithmic oxygen consumption which is indicative of microbial growth.

The data shows that the OS was used for the detection of microbial growth in the absence of direct broth to sensor contact. The detection delays observed in the vials without media are related to this particular test configuration. One having ordinary skill in this art would be able to optimize the parameters of the system, by example and not limitation, such as, by reducing the headspace volume and oxygen concentration which would result in improved sensitivity and make the measurements made without direct contact of liquid broth (gas phase) more comparable with the measurements made with contact of the liquid broth (liquid phase).

EXAMPLES 18-26

Methods and Materials: Oxygen Sensor Plate Preparation

Oxygen sensor plates were prepared by the general methods described herein. Falcon 1177 polystyrene 96 well U-bottom plates (BD Labware) were used for all experiments. The fluorescent dye Ru(DPP)$_3$Cl$_2$ was adsorbed to silica gel by rotary evaporation of ethanolic solutions of the dye with the silica gel. The adsorbed dye-silica and a moisture-cure clear silicone were mixed manually and immediately applied to plate wells with approximately 17 uL silicone per well. These were cured for 2-3 days in a controlled humidity incubator.

Microwell Plate Fluorescence Assays

All data was obtained with a BMG Polarstar fluorimeter at 37° C. using the bottom plate reading configuration. The bandpass filters were 465 nm for excitation and 590 nm for emission. For the experiments with MATRIGEL®, a Cytofluor 4000 fluorometer was used with a 485 nm excitation filter and a 580 nm emission filter. Data was read at selected time intervals. Normalized fluorescence data was generally obtained by dividing well values at selected time points by the same well's initial reading with only media or buffer present prior to adding cells.

Cells used for cytotoxicity and quantitation experiments (HL60, U937; ATCC) were grown in tissue culture media recommended by the supplier (RPMI; Gibco and ATCC, respectively). The media was supplemented with either 20% fetal bovine serum (Hyclone) for the HL60 cells or 10% FBS for the U937 cells, with the addition of penicillin, streptomycin and fungizone (Gibco) to prevent microbial contamination. Cells were maintained in a tissue culture incubator (37° C., 5% CO$_2$, 95% humidity) during all experiments between readings.

EXAMPLE 18

Quantitation of Fluorescent Signal vs. Cell Number for HL60 Cells Growing in Oxygen Sensor Plates HL60 cells (human promyelocytic leukemia cell line, ATCC #45500) were grown in tissue culture media recommended by the supplier (RPMI; Gibco), supplemented with 20% fetal bovine serum, heat inactivated at 50° C. for thirty minutes with the addition of penicillin, streptomycin and fungizone (Gibco) to prevent microbial contamination. Cells were maintained in tissue culture incubator (37° C., 5% CO$_2$, 95% humidity) during all experiments. Fluorescence of the oxygen sensor was read on a Polarstar™ fluorometer (BMG), using 465 nm excitation and 590 nm emission filters.

100 uL of tissue culture media was aliquoted into the wells of the Oxygen sensor plate and plate was allowed to equilibrate in the tissue culture incubator for 1 hour prior to taking the initial reading. This reading was used to normalize all subsequent readings to account for well to well variability. Cells were resuspended in fresh media at 960,000 cells/ml. Serial 1:2 dilution of this stock was performed and 100 uL of each dilution was alliquoted across the length of the plate in replicates of 12 (rows B-H), with final cell/well number from 1,500 to 96,000. In row A, 100 uL of tissue culture media was alliquoted into the wells in lieu of cells (no-cells control). Fluorescence measurements were taken every 24 hours over 5 days. The actual number of cells present was counted with a hemocytometer by sampling the parallel well (same seeding cell number). Mean fluorescence from 5 wells per data point (n=5) was plotted against the counted cell number (FIG. 10). Error bars are standard deviation of the mean.

EXAMPLE 19

Quantitation of Fluorescent Signal vs. Cell Number for U937 Cells Growing in Oxygen Sensor Plates This experiment was performed similarly to the one in Example 18. U937 cells (human histiocytic lymphoma cell line, ATCC, #CRL-1593.2) were grown as above, with the exception that 10% fetal bovine serum was used. Cell number varied from 750 to 48,000 cells per well. Fluorescence was measured at times indicated and plotted against seeded (initial) cell number (FIG. 11).

EXAMPLE 20

Cytotoxicity of Vinblastine Assayed By Oxygen Sensor

The experiment was performed as described in Example 18, with the following exceptions. Serial dilutions of vinblastine were prepared at twice the final concentration (100 nM to 0.1 nM) in tissue culture media. 100 uL of the drug dilution in tissue culture media was aliquoted across the width of the plate in replicates of five, reserving one column for no-drug (media only) control. After an initial reading, a constant number of cells (200,000/well) in 100 uL media were added to each well of rows A-E of the oxygen sensor plate, reserving rows F-H for no-cells control. Fluorescence was read at the indicated times. Mean fluorescence from 5 wells per data point (n=5) was plotted against vinblastine concentration (FIG. 12).

EXAMPLE 21

Cytotoxicity of Vinblastine Assayed by MTT

In parallel with the oxygen sensor assays, MTT assays were performed using a Cell Titer Kit™ (Promega), as in Example 20, with the following exceptions. For each time point (corresponding to oxygen sensor assay time point), one flat-bottom 96 well microtiter plate (Falcon) was used. 50 uL of drug dilution in tissue culture media was used for initial reading and cells were suspended in 50 uL media, to the final volume of 100 uL. At indicated time points, 10 uL of MTT reagent was added per well for 1 hour, after which 100 uL of the stop/lysis buffer was added. Plates were sealed with Parafilm™ and cell lysis occurred overnight. Absorbance (570 nm corrected by absorbance at 750 nm) was read using a Thermomax Microplate Reader (Molecular Devices). Mean absorbance from 5 wells per data point, with standard deviation as error bars, was plotted against vinblastine concentration (FIG. 13).

EXAMPLES 22-24

Cytotoxicity of Methotrexate, Sodium Azide, and SDS (Sodium Dodecyl Sulfate) Assayed by Oxygen Sensor Plates and MTT Assays These experiments was performed as described in Example 20, with the exception that appropriate dilutions of the above reagents were substituted for vinblastine: 0.01 nM to 10000 nM methotrexate, 0.00001 to 10 mM sodium azide, and 2 to 2000 uM SDS respectively. Complete dose response curves for these three additional drugs are shown, respectively in FIGS. 14, 15 and 16.

TABLE 11

Comparison of $IC_{50}$** Values For Selected Drugs With HL60 Cells Obtained With Oxygen Sensor Plates and MTT Assays

| | Time (hours) | | | | | | | | | |
|---|---|---|---|---|---|---|---|---|---|---|
| | 24 | | 48 | | 72 | | 96 | | 120 | |
| | $O_2$ Sensor | MTT | $O_2$ Sensor | MTT | $O_2$ Sensor | MTT | $O_2$ Sensor | MTT | $O_2$ Sensor | MTT |
| Vinblastine | * | * | 11 nM | 9 nM | 11 nM | 8 nM | 9 nM | 7 nM | 9 nM | 6.4 nM |
| Methotrexate | * | * | * | * | * | * | 19 nM | * | 12 nM | 14 nM |
| SDS | 340 uM | 500 uM | 300 uM | 440 uM | 300 uM | 430 uM | * | * | * | * |
| Sodium Azide | * | * | 13 uM | 25 uM | 13 uM | 25 uM | 9 uM | 3 uM | 5.8 uM | 1.6 uM |

*There was not a suitable sigmoidal dose response curve or that data were not sampled at this timepoint.
**50% Inhibitory Concentration.
This corresponds to Oxygen Sensor Experiments described in Examples 20 and 22-24.
MTT data was obtained by general methods described in Example 21.
The $IC_{50}$ values were determined as the concentration of drug that decreased the assay signal by 50%. $IC_{50}$ values were determined by a four-parameter logistic curve.

Discussion (for Table 11 and Examples 20-24): Cytotoxicity assays were performed in parallel with oxygen sensor plates and with standard MTT assays to measure the cytotoxicity of four drugs/toxins: vinblastine, methotrexate, sodium azide, and sodium dodecylsulfate. Both assay methods gave comparable $IC_{50}$ values at the selected timepoints. Because the MTT assay is an endpoint assay requiring additional reagents and destruction of the cells, it required a separate plate for each timepoint. The oxygen sensor assay, however, required only a single plate for all timepoint readings with each drug, significantly reducing the amount of labor and materials for each $IC_{50}$ determination over time.

Conclusion: For each timepoint in these cytotoxicity assays where significant drug or toxin effect could be measured, the $IC_{50}$ values obtained for the oxygen sensor plate matched closely with the MTT values.

EXAMPLE 25

Oxygen Consumption by Mammalian Cells Growing on MATRIGEL®

Various amounts (100 µl, 50 µl, 25 µl, or 0 µl) of MATRIGEL® (BD Labware cat. # 4024C) were added to the wells of an ice-cold $O_2$ sensor tray and then allowed to gel at room temperature. The plate was moved to a 37° C. incubator before use. MCD-1 cells (Moore et al. (1996) In Vitro Properties of a Newly Established Meulloblastoma Cell Line MCD-1. Mol. Chem. Neuropath. 29, 107-126) were suspended by trypsinization, washed with DMEM/F12 medium containing 10% fetal calf serum, and resuspended to $5 \times 10^5$ cells/ml in the same medium without serum. In some experiments, Hepes buffer (10 mM, pH 7.4) was added to better control the pH during the incubation period. Cells (100 µl, $5 \times 10^4$ cells) were added to the wells and the plate was moved to a modified PerSeptive Biosystems Cytofluor fluorimeter at 37° C. The fluorescence was read over time using 485 nm excitation and 580 nm emission filters.

There was a clear increase in fluorescence signal in wells containing MCD-1 cells compared to wells without cells (FIG. 17). The signal increased more slowly in wells containing increasing amounts of MATRIGEL®, suggesting there may be a barrier to the migration of cells toward the silicone sensor or to the diffusion of oxygen through the MATRIGEL®. Much of the increase in signal occurred over the first few hours of the experiment.

EXAMPLE 26

MCD-1, SK-N-SH, and NIH3T3 Cells Growing on MATRIGEL® Differ in Their Rates of Oxygen Consumption The $O_2$ sensor with or without 50 µl MATRIGEL® per well was prepared as described above. MCD-1, SK-N-SH (American Tissue Type Collection HTB11), or mouse fibroblast NIH3T3 cells (American Tissue Type Collection CRL1658) were collected by trypsinization, washed and added to wells as above at $5 \times 10^3$ or $5 \times 10^4$ cells per well. The plates were moved to a 37° C. fluorimeter and monitored as above.

Figure 18C:
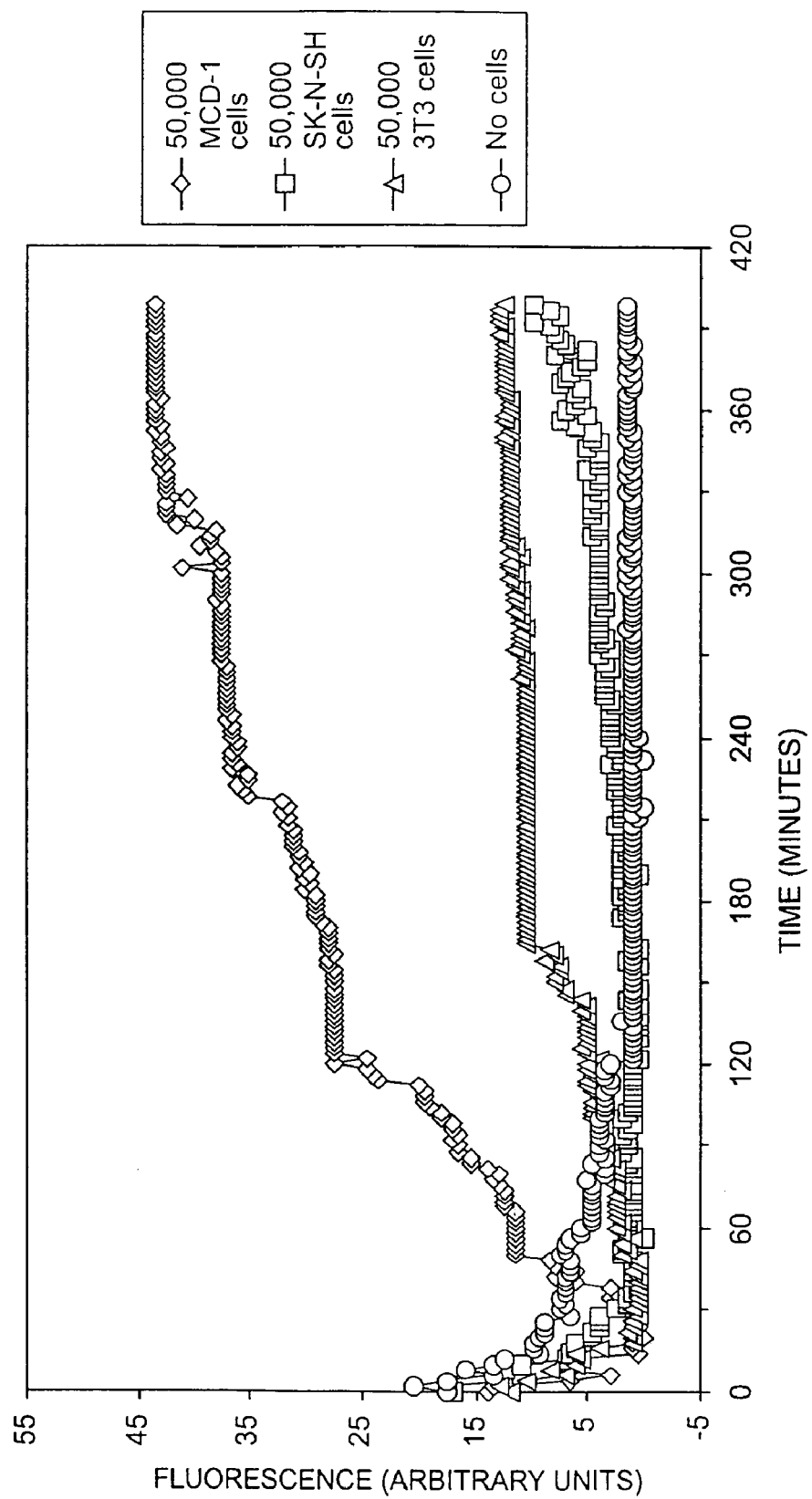

For MCD-1 cells (FIG. 18A), the fluorescence signal developed more slowly in the wells containing MATRIGEL® than in the wells lacking MATRIGEL®. However, the final levels of fluorescence were comparable. The signal with $5 \times 10^3$ MCD-cells per well was much smaller than the signal with $5 \times 10^4$ cells, but was above the "no cells" control. In addition, the oxygen consumption by the MCD-1 cells was inhibited by 0.1% sodium azide, as also observed for suspension cell cultures. The signal with $5 \times 10^5$ SK-N-SH cells (FIG. 18B) was very clearly above background and moreover, appeared to show a second increase beginning at about 6 hr, perhaps due to cell division. A third cell line, 3T3, showed an oxygen consumption between that of MCD-1 and SK-N-SH cells (FIG. 18C). Although the three cell lines differ markedly in their metabolic rates, oxygen consumption could be detected in all cases by a proper choice of cell number.

Table 12 presents a summary for some of the mammalian cell types and corresponding conditions for growth which have been used with oxygen sensor plates.

TABLE 12

Cell lines which have been tested in Oxygen Sensor Plates

| Cell Line | Cell type | Media | Contains | Supplements |
|---|---|---|---|---|
| Adherent Cells | | | | |
| SK-N-SH | Human neuroblastoma | S-MEM Gibco cat # 11380 Contains | Eagles Salts L-glutamine | Pen/Strep/Fungizone Nonessential Amino Acids Sodium Pyruvate 10% Fetal Bovine Serum |
| MCD-1 | Human Medulloblastoma | D-MEM F12 Gibco Cat # 11330 | 15 mM Hepes L-glutamine pyrodoxine HCl | Pen/Strep/Fungizone 10% Fetal Bovine Serum |
| WI-38 | Human Fibroblast embroyonic lung | MEM Gibco cat # 11095 | Earles Salts L-glutamine | Pen/Strep/Fungizone Nonessential Amino Acids Sodium Pyruvate 10% Fetal Bovine Serum |
| NIH-3T3 | Mouse Fibroblast | D-MEM F12 Gibco cat # 11330 | 15 mM Hepes L-glutamine pyrodoxine HCl | No supplements |
| Nonadherent Cells | | | | |
| HL60 | Human promyelocytic leukemia | RPMI Gibco cat # 11875 | L-glutamine | Pen/Strep/2X Fungizone 20% Fetal Bovine Serum, heat inactivated |
| U-937 | Human histiocytic lymphoma | RPMI Gibco cat # 11875 | L-glutamine | Pen/Strep/2X Fungizone 10% Fetal Bovine Serum |
| | | ATCC cat # 30-2001 | 10 mM Hepes 1 mM Na pyruvate 4 g/L glucose 1.5 g/L bicarbonate 2 mM glutamine | Pen/Strep/2X Fungizone 10% Fetal Bovine Serum |

EXAMPLE 27

Oxygen Sensor Added to Bottom of Well Insert Membrane

This example demonstrates an alternate format for using the sensors to monitor cells and provides a method for monitoring the growth of an adherent cell line (MDCK) by applying the sensor to the exterior of a cell culture insert membrane which supports growth of adherent cells.

The oxygen sensor silicone formulation was prepared by the general methods described herein and 50 uL was applied to one half of the wells of a 24 well microplate (Falcon product 3047). In addition, 20 uL of the sensor silicone mixture was added to the exterior side of the track-etched PET (polyethylene terephthalate) membrane of 24-well plate inserts (Falcon 3097). These sensors were cured at 37° C. for 2 days.

Cells in these modified inserts were monitored in the unmodified wells of the 24 well plate and compared to corresponding cell lines grown in modified wells with the sensor on the well bottom but without an insert present. Cells were grown and monitored by fluorescence as in the preceding examples. Briefly, 300,000 HL60 cells were added to each modified insert or well and 100,000 MDCK cells were added to each insert or well. The cells were added in the corresponding media for each cell type (see Table 12): 0.7 mL per well and 0.3 mL per insert. Control wells with media only and no cells were also monitored. Readings were taken daily for nine days.

Figure 19A:
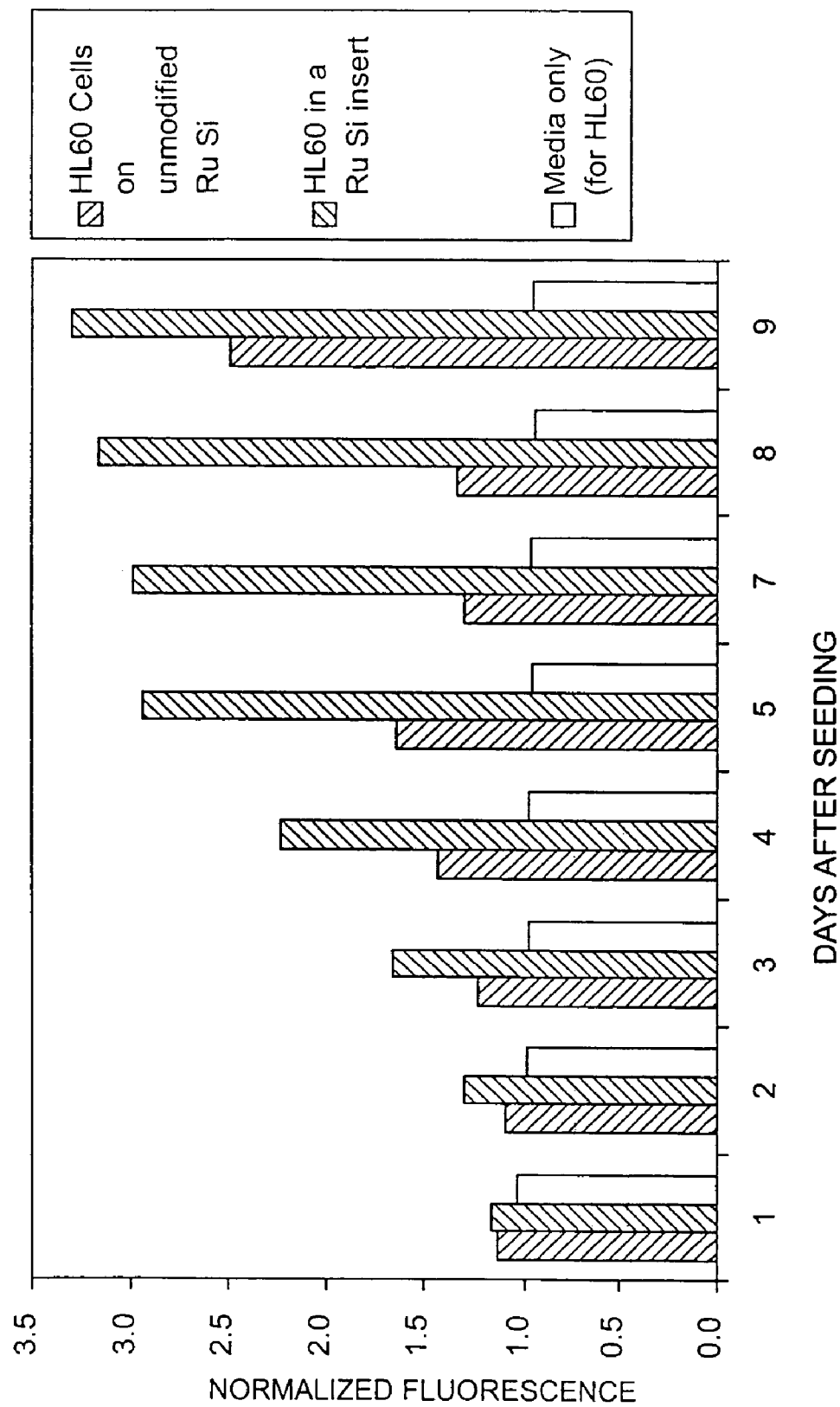
FIG. 19A graphically depicts relative changes in the intensity of fluorescence over time for HL60 cells grown in a 24-well plate (i) with the sensor on the bottom of the well (unmodified RuSi); (ii) with the sensor on the bottom of an insert. The third data set is for a control of media only with no cells.
Figure 19B:
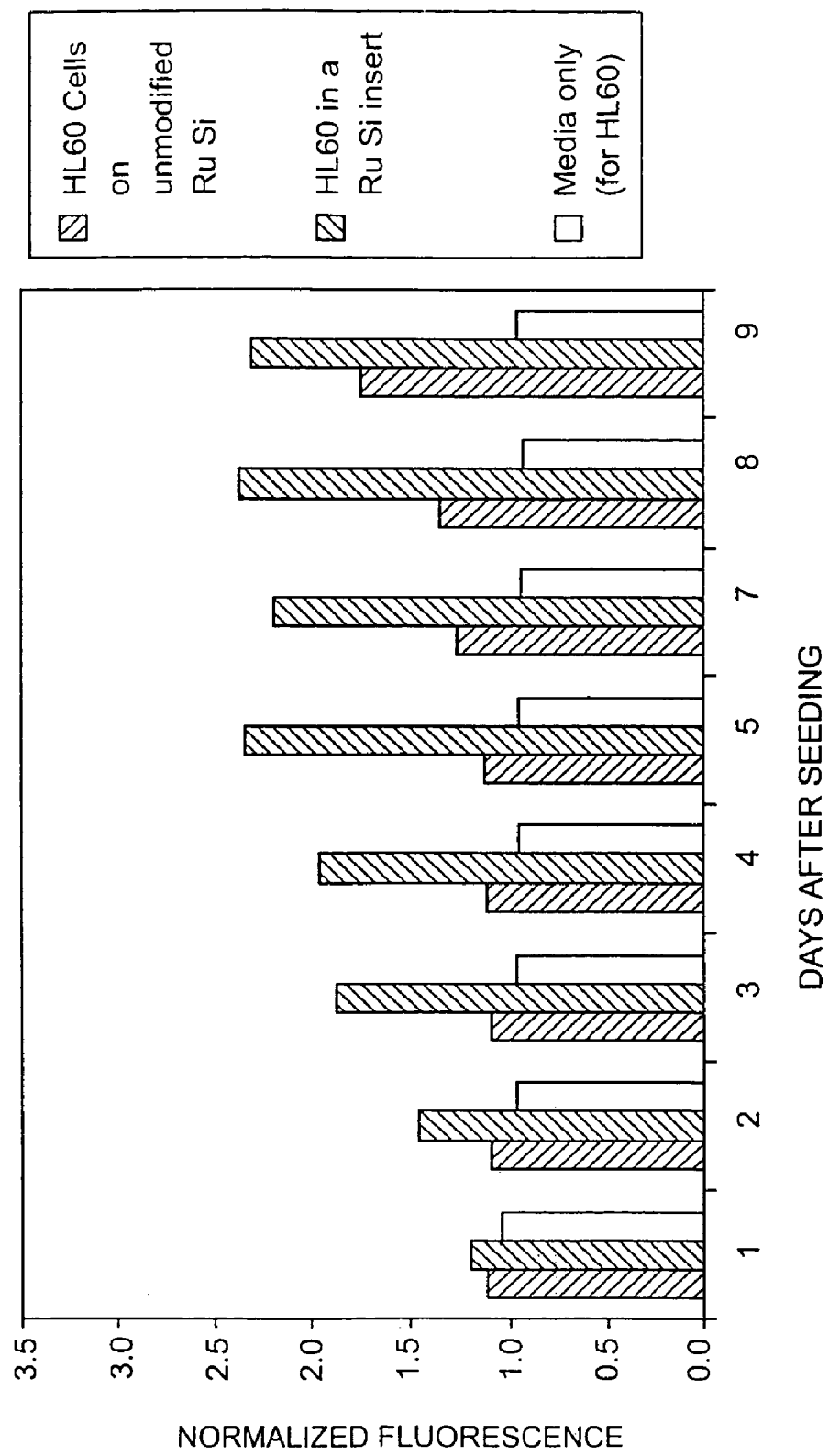
FIG. 19B shows the same experiments as in FIG. 19A, but using adherent cell line MDCK instead of HL60 cells.

The results are shown in FIGS. 19A and 19B. For both the adherent cells and non-adherent cells a greater signal was obtained more quickly with the modified insert sensors.

EXAMPLE 28

Preparation of a 384 Well Sensor Plate

The general methods described above and in Example 18 were used to prepare a 384 well sensor plate (Nunc #242765 clear polystyrene) with 10 uL of sensor per well. A titration of HL60 cells in 100 uL media was monitored with the BMG fluorescence plate reader.

Figure 20:
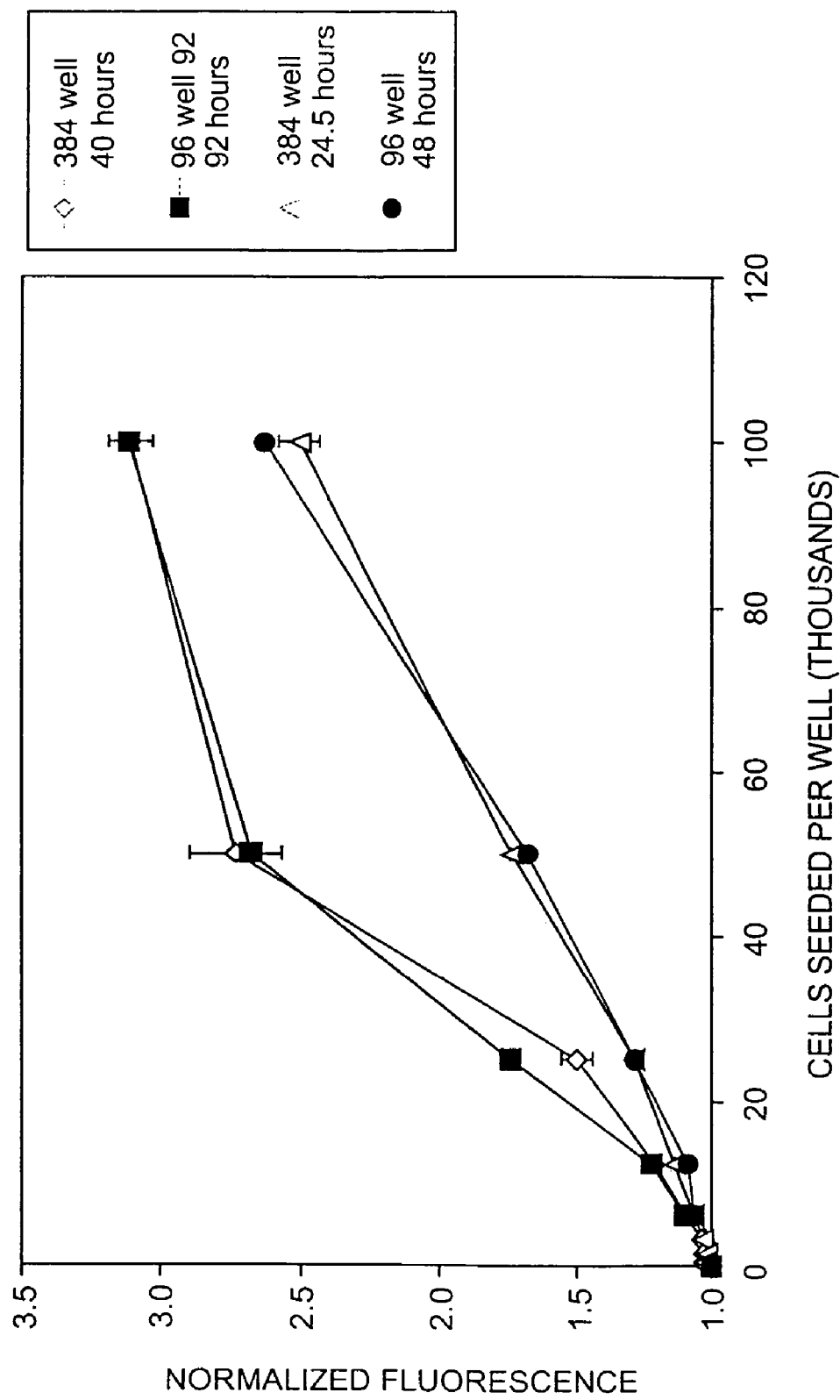
FIG. 20 graphically depicts the normalized fluorescence intensity vs. the number of HL60 cells, grown in 96 well oxygen sensor plates and in 384 well sensor plates.

The results are shown in FIG. 20 and compared to the corresponding 96 well plate results. The 384 well plate demonstrated an improved time-to-signal response for the same number of HL60 cells per well.

EXAMPLE 29

Detection of SF-9 Insect Cell Growth

SF-9 insect cells are derived from the pupal ovarian tissue of the fall army worm, *Spodoptera frugiperda* (D. R. O'Reilly, et al (1992) *The Baculovirus System: A Laboratory Guide*, Chapman and Hall, NYC, N.Y.). A 96 well oxygen sensor plate was equilibrated for 1 hour at 27° C. with 100 μL TMN-FH media (Invitrogen, Inc., Graces Insect media supplemented with 10% fetal calf serum, and powdered form of yeastolate, lactalbumin hydrolysate and glutamine).

Seven concentrations of serially diluted SF-9 cells were added in replicates of five across the $O_2$ sensor plate starting at 160,000 cells/well (800,000 cells/mL) down to 1,500 cells/well (7,500 cells/mL). Cells were incubated at 27° C. in a humidity chamber and fluorescence was monitored over time using the same instrument and parameters used in the mammalian cell experiments.

Figure 21:
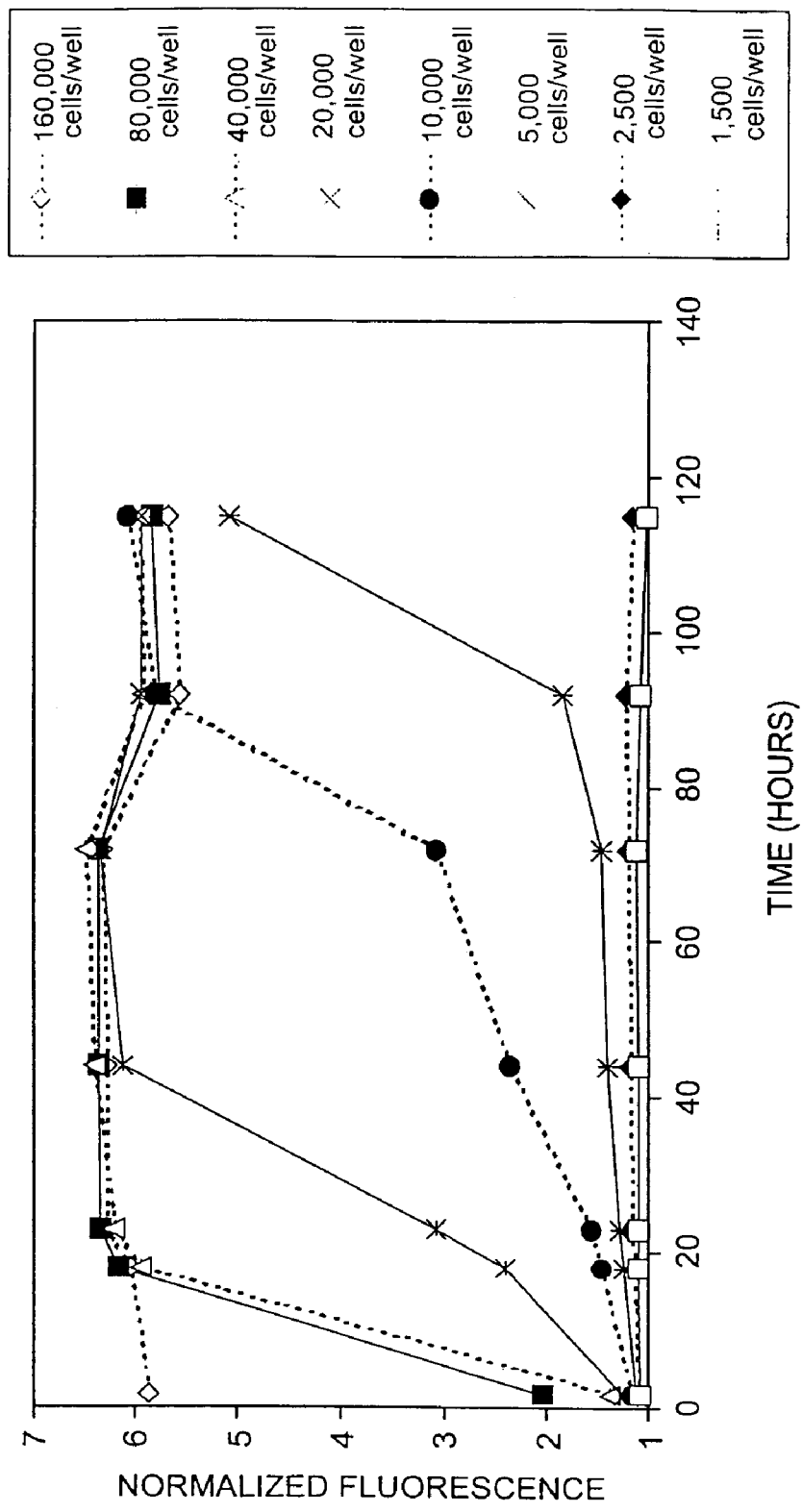
FIG. 21 graphically depicts relative changes in the intensity of fluorescence by plotting fluorescence vs. time for SF-9 insect cells grown at the indicated concentrations in a 96 well oxygen sensor plate.

The signal increased more rapidly and to a greater degree than mammalian cells (FIG. 21). The wells with 160,000 cells/well reached maximum fluorescence within 2 hours. As with other cellular experiments, the initial cell number in a well can be estimated by the time required to reach a measurable fluorescence increase per well.

EXAMPLE 30

Monitoring Yeast Growth

Growth of a sample of *Saccharomyces cerevisiae* was monitored in a 96 well oxygen sensor plate (prepared as described in Example 16). An initial yeast broth was prepared by hydrating 11.5 g of dried Edme Ale Yeast (Edme, Ltd., UK) in 100 mL water at 37° C. for 30 minutes. This yeast slurry was added to a 500 mL mixture of NZCYM Media (BBL #99165) plus 10 g/L d-glucose. After 36 hours of fermentation at 27° C. Oust past exponential growth phase) the yeast cell concentration was determined using a hemacytometer. Serial dilutions were prepared from $1.2 \times 10^7$ cells/mL down to $1.6 \times 10^4$ cells/mL in fresh NZCYM broth with either 10, 50, 100, or 200 g/L d-glucose. Each suspension was measured in triplicate (200 uL/well) in a 96 well sensor plate at 27° C. with continuous readings every 400 sec for 13.3 hours.

Figure 22:
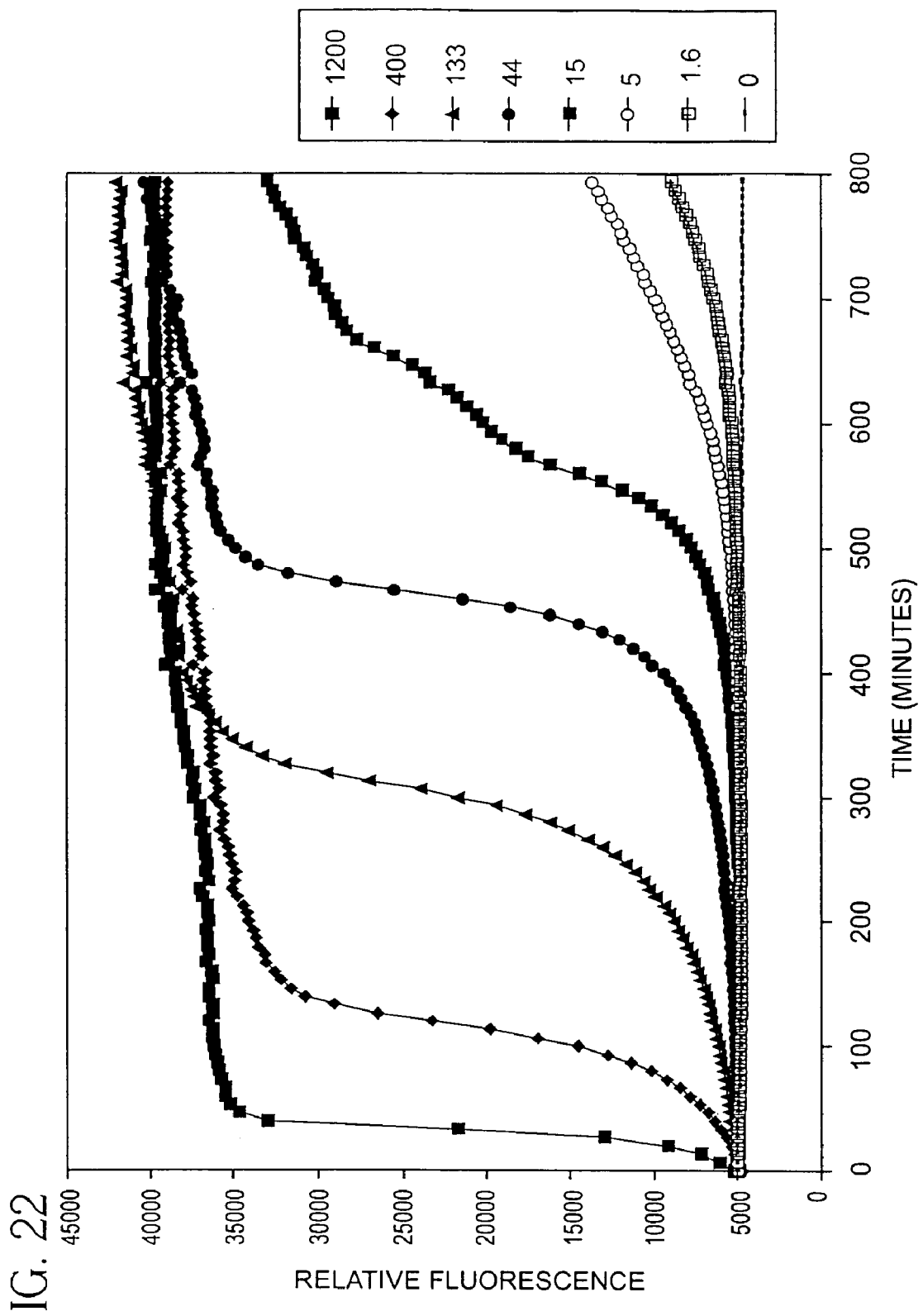
FIG. 22 graphically depicts relative changes in the intensity of fluorescence by plotting fluorescence vs. time for yeast cells grown at the indicated concentrations in a 96 well oxygen sensor plate.
Figure 23:
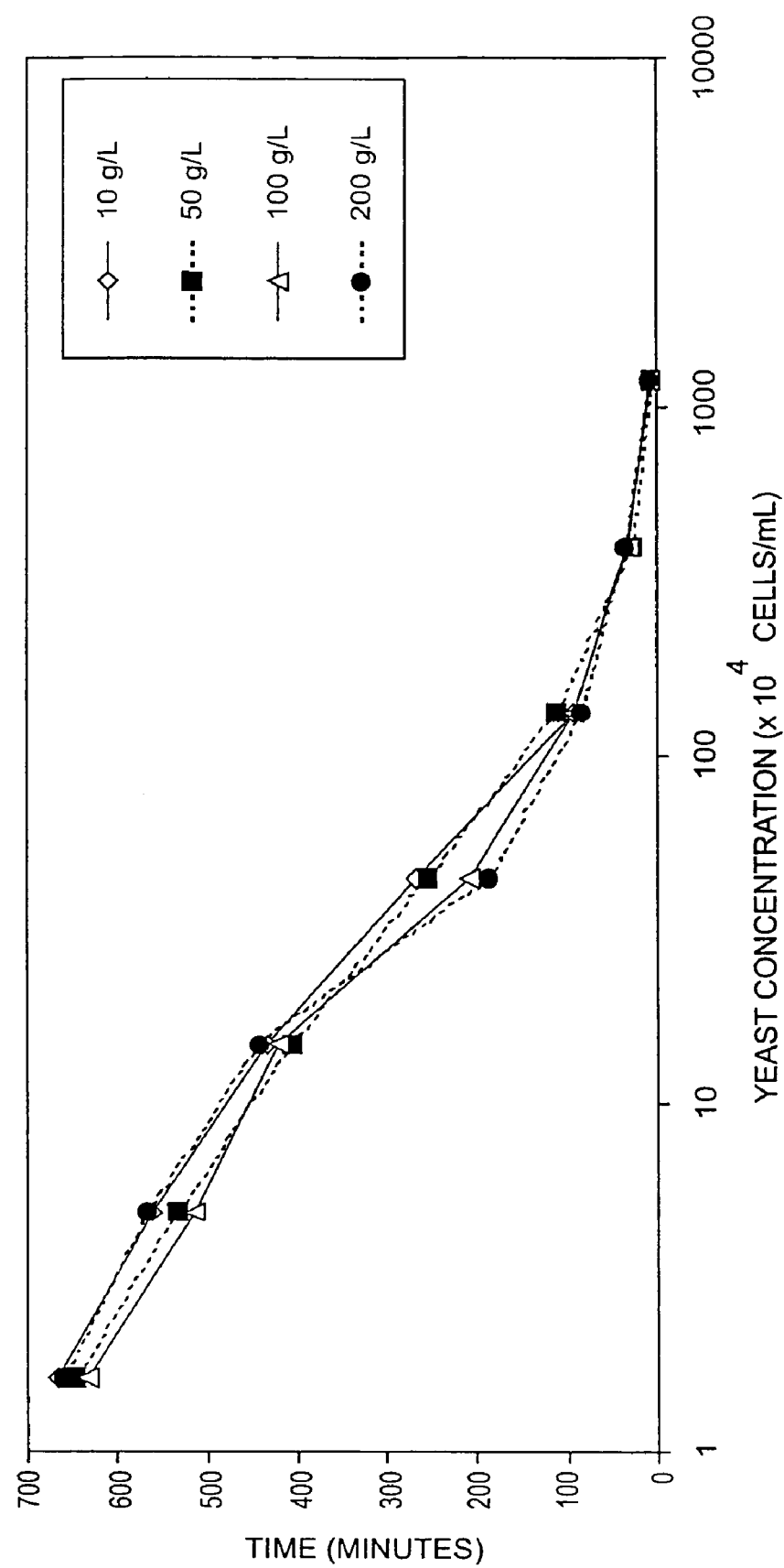
FIG. 23 graphically depicts the relationship between the initial concentration of yeast cells and the time required to reach 120% of the initial fluorescence signal for yeast growing in media with the four indicated glucoase concentrations.

FIG. 22 shows the fluorescence signal for the yeast cell titration in 10 g/L glucose. This indicates the relationship between initial concentration and time required to generate a positive signal. FIG. 23 compares yeast growth (as determined by time required to reach 120% of initial fluorescence) vs. glucose concentration. The two lower glucose concentrations (10 and 50 g/L) indicate a more linear relationship to the initial yeast concentration, whereas the two higher glucose concentrations (100 and 200 g/L) appear to retard initial growth of low yeast concentrations. This demonstrates one way the sensor plates can be used for optimizing cellular growth conditions.

It is apparent that many modifications and variations of this invention as hereinabove set forth may be made without departing from the spirit and scope of the present invention and the above examples are not intended to in any way limit the present invention but are merely exemplary.

What is claimed is:

1. A method for determining oxygen consumption by cells comprising the steps of:
   providing a sample comprising a mammalian cell culture;
   placing the sample in chemical communication with a sensor composition which comprises a luminescent compound that exhibits a change in luminescent property, upon exposure to oxygen, wherein the presence of the sensor composition is nondestructive to the mammalian cells;
   irradiating the sensor composition with light containing wavelengths which cause the luminescent compound to luminescence; and
   determining the change in luminescent property, over a period of time, wherein the change in luminescent property is indicative of a change in oxygen consumption by the mammalian cells.

2. The method of claim 1, further comprising the step of: comparing the determined change in luminescent property to a control.

3. The method of claim 1 wherein the luminescent compound is contained within a matrix that is relatively impermeable to water and non-gaseous solutes, but which has a high permeability to oxygen.

4. The method of claim 3, wherein the matrix is a rubber or plastic matrix.

5. The method of claim 3, wherein the matrix is a silicone rubber matrix.

6. The method of claim 1, wherein the luminescent compound is adsorbed on solid silica particles.

7. The method of claim 1, wherein the luminescent compound is a tris-4,7-diphenyl-1,10-phenanthroline ruthenium (II) salt.

8. The method of claim 7, wherein the luminescent compound is tris-4,7-diphenyl-1,10-phenanthroline ruthenium (II) chloride.

9. The method of claim 1, wherein the luminescent compound is a tris-2,2'-bipyridyl ruthenium (II) salt.

10. The method of claim 9, wherein the luminescent compound is tris-2,2'-bipyridyl ruthenium (II) chloride hexahydrate.

11. The method of claim 1, wherein the luminescent compound is 9,10-diphenyl anthracene.

12. The method of claim 1, wherein the sample is exposed to atmospheric oxygen.

13. The method of claim 1, wherein, the sample is also contacted with one or more extracellular matrices.

14. The method of claim 13, wherein the extracellular matrix is collagen.

15. The method of claim 1, wherein the period of time is not greater than approximately 6 hours.

* * * * *